(12) United States Patent
Banerjee et al.

(10) Patent No.: US 11,846,638 B2
(45) Date of Patent: Dec. 19, 2023

(54) METHODS FOR DETECTING NA/K-ATPASE-MEDIATED SRC SIGNALING FOR DIAGNOSIS AND PROGNOSIS OF CANCER

(71) Applicant: Marshall University Research Corporation, Huntington, WV (US)

(72) Inventors: Moumita Banerjee, Huntington, WV (US); Xiaoyu Cui, Huntington, WV (US); Zijian Xie, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 214 days.

(21) Appl. No.: 16/640,617

(22) PCT Filed: Sep. 6, 2018

(86) PCT No.: PCT/US2018/049755
§ 371 (c)(1),
(2) Date: Feb. 20, 2020

(87) PCT Pub. No.: WO2019/051090
PCT Pub. Date: Mar. 14, 2019

(65) Prior Publication Data
US 2020/0191790 A1    Jun. 18, 2020

Related U.S. Application Data

(60) Provisional application No. 62/554,669, filed on Sep. 6, 2017.

(51) Int. Cl.
*G01N 33/574* (2006.01)
*G01N 33/68* (2006.01)

(52) U.S. Cl.
CPC ... *G01N 33/57415* (2013.01); *G01N 33/6872* (2013.01); *G01N 2333/914* (2013.01); *G01N 2440/14* (2013.01)

(58) Field of Classification Search
CPC ......... G01N 33/57415; G01N 33/6872; G01N 2333/914; G01N 2440/14; G01N 2800/52; G01N 33/57434; G01N 33/57438
See application file for complete search history.

(56) References Cited

U.S. PATENT DOCUMENTS

| | | | |
|---|---|---|---|
| 7,999,080 B2 | 8/2011 | Hornbeck et al. | |
| 9,139,864 B2 | 9/2015 | Krizman | |
| 2017/0183639 A1* | 6/2017 | Xie | A61K 38/46 |

FOREIGN PATENT DOCUMENTS

WO    2015/160529 A1    10/2015

OTHER PUBLICATIONS

Cui et al 2016 (Regulation of Cellular Bioenergetics by Na/K-ATPase, Dissertation—University of Toledo, Nov. 2016), (Year: 2016).*
Holthouser et al (2009) (Ouabain stimulates Na—K-ATPase through a sodium/hydrogen exchanger-1 (NHE-1)-dependent mechanism in human kidney proximal tubule cells, American Journal of Physiology, Renal Physiology, vol. 299, 2009). (Year: 2009).*
Soltoff et al (Journal of Biological Chemistry, 2010, 285:36330-36338) (Year: 2010).*
Banerjee (Dissertation: A Model for Domain-Specific Regulation of Src kinase by alpha-1 subunit of Na/KATPase. The University of Toledo. ProQuest Dissertations Publishing, 2013. 3613224 (Year: 2013).*
Heibeck et al (J. Proteome Res. 2009, 8:3852-3861) (Year: 2009).*
European Patent Office, Supplementary European Search Report issued in corresponding Application No. EP 18852931.7 dated Apr. 13, 2021.
Banerjee, M., et al. "Na/K-ATPase Y260 Phosphorylation-mediated Src Regulation in Control of Aerobic Glycolysis and Tumor Growth," Scientific Reports, vol. 8, No. 1, Aug. 17, 2018, pp. 1-13.
Banerjee, M. "A Model for Domain-Specific Regulation of Src kinase by alpha-1 subunit of Na/K-AtPase," The University of Toledo, Dec. 2013, XP002771815, [retrieved on Jul. 6, 2017].
United States Patent and Trademark Office, International Search Report and Written Opinion issued in corresponding Application No. PCT/US2018/049755, dated Dec. 21, 2018.
Ayoub, E., et al. "Regulation of the Src Kinase-associated Phosphoprotein 55 Homologue by the Protein Tyrosine Phosphatase PTP-PEST in the Control of Cell Motility," The Journal of Biological Chemistry, Jul. 29, 2013, vol. 288, No. 36, pp. 25739-25743.

\* cited by examiner

*Primary Examiner* — Laura B Goddard
*Assistant Examiner* — Sarah A Alsomairy
(74) *Attorney, Agent, or Firm* — Stites & Harbison, PLLC; Terry L. Wright

(57) ABSTRACT

Methods for diagnosis or prognosis of a cancer in a subject are provided and include the steps of: obtaining a biological sample from a subject; determining an amount of a phosphorylation at a Y260 residue in a Na/K ATPase present in the biological sample; and comparing the amount of the phosphorylation in the sample to a control level to thereby diagnose the cancer. Methods for detecting a metabolic switch from oxidative phosphorylation to aerobic glycolysis are also provided in which a biological sample including one or more cells is obtained and an amount of a phosphorylation at a Y260 residue in a Na/K ATPase is determined in the one or more cells.

9 Claims, 37 Drawing Sheets

| Na/K-ATPase Isoform | Y260 position |
|---|---|
| Human α1 | 256 RGIVVYTGDRT 265 |
| Human α2 | 253 RGIVIATGDRT 263 |
| Human α3 | 245 RGVVVATGDRT 255 |
| Human α4 | 263 RGIVIATGDST 273 |

KSSKIMESFK NMVPQQALVI RNGEKMSINA EEVVVGDLVE VKGGDRIPAD LRIISANGCK VDNSSLTGES
EPQTRSPDFT NENPLETRNI AFFSTNCVEG TARGIVVYTG DRTVMGRIAT LASLEGGT PIAAEI

IF: α1 Na/K-ATPase

| Upregulated gene | GENE name | log2 ratio | AAC19 FPKM | Y260A FPKM | p value | FDR value |
|---|---|---|---|---|---|---|
| PDK1 | pyruvate dehydrogenase kinase 1 | 0.43 | 36.77 | 49.64 | 3.09E-03 | 7.21E-03 |
| PDK4 | pyruvate dehydrogenase kinase 4 | 1.08 | 1.89 | 4.01 | 1.70E-03 | 4.20E-03 |
| HK2 | Hexokinase 2 | 0.43 | 39.68 | 53.47 | 3.30E-06 | 1.21E-05 |
| LDHA | Lactate Dehydrogenase A | 0.32 | 1230.09 | 1534.50 | 8.14E-40 | 1.38E-38 |
| SLC2A4 | GLUT4 | 0.77 | 2.86 | 4.89 | 3.20E-02 | 5.88E-02 |
| GOT1 | Aspartate aminotransferase | 0.58 | 129.48 | 193.20 | 4.90E-20 | 4.82E-19 |
| SLC7A7 | basic amino acid transporter | 0.32 | 21.57 | 26.93 | 4.60E-02 | 8.24E-02 |
| SLC7A3 | cationic amino acid transporter | 0.77 | 4.99 | 8.52 | 7.27E-03 | 1.57E-02 |
FIG. 11D
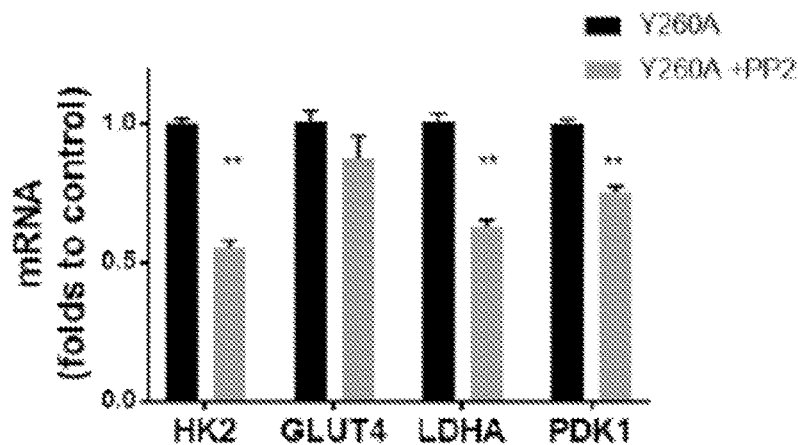
FIG. 11E
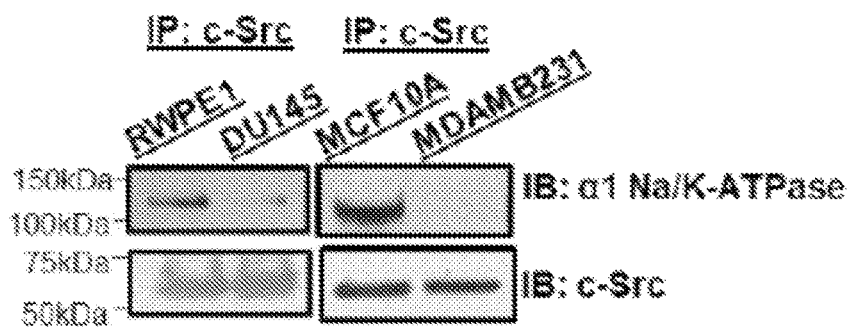
FIG. 12A

METHODS FOR DETECTING NA/K-ATPASE-MEDIATED SRC SIGNALING FOR DIAGNOSIS AND PROGNOSIS OF CANCER

RELATED APPLICATIONS

This application claims priority from U.S. Provisional Application Ser. No. 62/554,669, filed Sep. 6, 2017, the entire disclosure of which is incorporated herein by this reference.

TECHNICAL FIELD

The presently-disclosed subject matter relates to methods for detecting Na/K-ATPase-mediated Src signaling for diagnosis and prognosis of cancer. In particular, certain embodiments of the presently-disclosed subject matter relate to methods for detecting Na/K-ATPase-mediated Src signaling for diagnosis and prognosis of cancer that are based on Na/K-ATPase phosphorylation.

BACKGROUND

Cancer cells show increased dependence on aerobic glycolysis for energy utilization, a phenomenon known as Warburg effect. This metabolic switch provides important metabolites for cancer cells. The proto-oncogene Src kinase is known to drive the Warburg effect in cancer cells by phosphorylating metabolic enzymes and is frequently hyper-activated in cancer. Although a lot is known about the structural regulation of Src activity, it is not sufficient to explain this apparent hyper-activation in cancer. To date, a plasma membrane regulator of Src has not been identified where Src participates in transmitting signals from multiple cell surface receptors.

The Na/K-ATPase is a highly expressed membrane protein and the plasma membrane contains more than a million of them in most human cells. Interestingly, only about 30% of the plasma membrane Na/K-ATPase is engaged in ion pumping. Recent studies have uncovered that the $\alpha 1$ Na/K-ATPase interacts with Src to form a receptor complex that allows endogenous cardiotonic steroids (CTS) to initiate protein and lipid kinase cascades through EGF receptor/reactive oxygen species (ROS) pathways, thereby regulating an array of cellular activities. However, whether this interaction is important for the regulation of the plasma membrane pool of Src is unknown.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes methods for detecting Na/K-ATPase-mediated Src signaling for diagnosis and prognosis of cancer. In particular, certain embodiments of the presently-disclosed subject matter include methods for detecting Na/K-ATPase-mediated Src signaling for diagnosis and prognosis of cancer that are based on Na/K-ATPase phosphorylation. In some embodiments, a method for diagnosis or prognosis of a cancer in a subject is provided that comprises the steps of: obtaining a biological sample; determining an amount of a phosphorylation at a Y260 residue in a Na/K ATPase present in the biological sample; and comparing the amount of the phosphorylation in the sample, if present, to a control level of the phosphorylation, wherein the subject is diagnosed as having a cancer or a risk thereof if there is a reduction in the amount of the phosphorylation in the sample as compared to the control level. In some embodiments, the Na/K ATPase is an $\alpha 1$ Na/K ATPase isoform. In some embodiments, the cancer is a prostate cancer, a kidney cancer, or a breast cancer, or other types of cancer. In some embodiments, the cancer is a metastatic cancer.

With respect to the biological sample used to determine the phosphorylation of the Y260 residue, in some embodiments, the biological sample comprises blood, plasma, or serum. In some embodiments, the biological sample includes one or more cancer or tumor cells, such as, in certain embodiments, one or more tumor cells from a tumor biopsy. In some embodiments, the biological sample is obtained from a subject, such as a human subject.

In some embodiments, determining the amount of phosphorylation at the Y260 residue in the Na/K ATPase comprises determining an amount of phosphorylation using mass spectrometry (MS) analysis, immunoassay analysis (e.g., ELISA), or both or all of the foregoing. In some embodiments, a treatment for the cancer can be selected or modified based on the determined amount of phosphorylation of the Y260 residue. In some embodiments, a chemotherapeutic or other anti-cancer agent can then be administered to the subject subsequent to diagnosing the subject as having a cancer or a risk thereof. In some embodiments, an amount of Src activity can also be measured in the biological sample as an additional diagnostic or therapeutic indicator.

Further provided, in some embodiments of the presently-disclosed subject matter are methods for detecting a metabolic switch from oxidative phosphorylation to aerobic glycolysis. In some embodiments, such detection methods include the steps of: obtaining a biological sample including one or more cells; and determining an amount of phosphorylation of a Y260 residue in a Na/K ATPase present in the one or more cells. In some embodiments, the detection methods further include a step of determining an amount of lactate produced in the one or more cells and/or a step of comparing the amount of phosphorylation, if present, to a control level where a reduction in the amount of phosphorylation indicates the metabolic switch. In some embodiments, the Na/K ATPase is an $\alpha 1$ Na/K ATPase isoform. In some embodiments, the one or more cells comprises a cancer cell, such as, in certain embodiments, a prostate cancer cell, a kidney cancer cell, or a breast cancer cell.

Further features and advantages of the presently-disclosed subject matter will become evident to those of ordinary skill in the art after a study of the description, figures, and non-limiting examples in this document.

BRIEF DESCRIPTION OF THE DRAWINGS

(FIG. 1A) a table showing a comparison of Y260 containing sequences in second cytoplasmic domain (CD2) of different human Na/K-ATPase isoforms; (FIG. 1B) images showing the interaction between CD2 and Src in different cell lines, where representative blots are shown; (FIG. 1C) images and a graph showing the effects of ouabain on ERK activation (*p<0.05 compared with vehicle-treated control of the same cell line (Student's T-test); #p<0.05 compared between different cell lines (One-way ANOVA)); (FIG. 1D) images showing the detection of Y260 phosphorylation in CD2, where representative blots are shown; (FIG. 1E) images showing Y260 phosphorylation and expression of α1 Na/K-ATPase in mouse tissues, where representative blots are shown.

(FIG. 2A) images showing Y260 phosphorylation in purified pig kidney α1 Na/K-ATPase (2 μg) by Src (4.5 units) in presence of 2 mM $Mg^{2+}$-ATP in 10 minutes, where representative blots are shown with control blots showing Src phosphorylation at Y418 and Y529 sites by $Mg^{2+}$-ATP; (FIG. 2B) images showing the effects of PP2 (5 μM, 30 minutes) on tyrosine phosphorylation of α1 Na/K-ATPase in LLC-PK1 cells, where a representative immunoblot is shown; (FIG. 2C) images showing the effects of Src family kinase knockout on Y260 phosphorylation, where cell lysates were prepared from Src, Yes, Fyn knockout SYF, and Src-rescued SYF cells and representative blots are shown; (FIG. 2D) images and graphs showing the effects of ouabain on Y260 phosphorylation as a function of time in LLC-PK1 cells (**p<0.01 compared with vehicle-treated control); (FIG. 2E) images showing the effects of different concentrations of ouabain on Y260 phosphorylation in LLC-PK1 cells; (FIGS. 2F and 2G) images showing the effects of recombinant EGF on Y260 phosphorylation in LLC-PK1 cells on time—(FIG. 2F) and dose—(FIG. 2G) dependent manner, where representative immunoblots are shown, and (FIG. 2H) images showing the effects of integrin signaling on Y260 phosphorylation, where cell attachment-induced integrin signaling was measured by plating cells on fibronectin-coated dishes and representative blots are shown.

(FIGS. 3A-3C) images and graphs showing the effects of Y260A mutation on ouabain-induced signaling, where AAC-19 (control) and Y260A mutant cells were treated with different concentrations of ouabain for 10 minutes and cell lysates were collected and analyzed for Src activation (pY418Src/c-Src) (FIG. 3A), ERK activation (pERK1/2/ERK1/2) (FIG. 3B), and Akt activation (pS473Akt/Akt) (FIG. 3C) (*p<0.05 and p<0.01 compared with vehicle-treated AAC-19 control, ##p<0.01 compared with vehicle-treated Y260A control, and ••p<0.01 between different cell lines in the same treatment dose as indicated (Two-way ANOVA). n=4-5); (FIG. 3D) images and a graph showing α1 Na/K-ATPase/Src interaction analyzed by immunoprecipitation (p<0.01 compared with AAC-19 (Student's T-test)); (FIG. 3E) images and graphs showing the effects of Y260A mutation on EGF signaling assessed by Src activation and EGFR activation, where representative blots and quantifications are shown and the same statistical symbols are used as in (FIGS. 3A-3C)

(FIG. 4A) a graph showing lactate production from culture media of AAC-19 and Y260A mutant cells (**p<0.01 compared with control AAC-19 cells); (FIG. 4B) a graph showing the effects of different concentrations of 2-DG on cellular ATP content (*p<0.05 and **p<0.01 compared with vehicle-treated control (same cell line) (One-way ANOVA)); (FIG. 4C) a graph showing the effects of glucose removal on cell growth, where cell number was counted and presented as folds of change (*p<0.05 and p<0.05 compared with 0 hour in the same cell line (One-way ANOVA)); (FIG. 4D) a graph showing bioenergetic parameter ECAR measurements of AAC-19 and Y260A cells, where an actual representative trace of 4-7 separate measurements is presented; (FIG. 4E) a graph showing glycolytic reserve capacity and lactate-related ECAR calculated from the experiments presented in FIG. 4D as marked (p<0.01 compared with AAC-19 cells (Student's T-test)); (FIG. 4F) a graph showing bioenergetic parameter-OCR measurements of AAC-19 and Y260A mutant cells, where spare capacity was calculated from OCR measurements (*p<0.05 compared with AAC-19 cells (Student's T-test)); (FIG. 4G) a graph showing lactate production from culture medium of Y260A cells in the presence or absence of 5 μM PP2 for 4 h (**p<0.01 compared with Y260A control); and (FIG. 4H) a graph showing ECAR measurement in Y260A cells cultured in the presence or absence of 5 μM PP2 for 4 h.

(FIG. 5A) images and graphs showing the measurement of Y260 phosphorylation in cancer cell lines, where cell lysates from a panel of prostate (LNCAP, DU145, and PC3) and breast (MCF7, MDAMB231, and BT-20) cancer cell lines were compared with corresponding control cells (prostate RWPE1 and breast MCF10A), for Na/K-ATPase α1 expression and Y260 phosphorylation. (p<0.01 compared with respective normal cell line (Unpaired T-test, Welch's test)); (FIG. 5B) images and a graph showing interaction between Src and α1 Na/K-ATPase in control DU-P1 and knock-down A4-7 cells analyzed by immunoprecipitation (p<0.01 compared with DU-P1 (Student's T-test)); (FIG. 5C) images and a graph showing the effects of α1 Na/K-ATPase knock-down on Src activity, FAK activity and Myc, analyzed by immunoblots, where representative immunoblots are shown and quantitative data from 4-5 separate experiments are presented (*p<0.05 and **p<0.01 compared with DU-P1 (Student's T-test)); (FIG. 5D) graphs showing the measurement of lactate in medium from DU-P1 and A4-7 cell culture (left panel) and in medium from A4-7 cells cultured in the presence or absence of 5 μM PP2 for 4 h (right panel) (*p<0.05 compared with DU-P1 (left panel) or A4-7 without PP2 treatment (right panel) (Student's T-test)); (FIG. 5E) a graph showing cell proliferation rate of DU-P1 vs. A4-7 in 48 hours (left panel) and PP2 inhibition of A4-7 proliferation at 48-hour (right panel) (p<0.05 and p<0.01 compared with DU-P1 24 h, ##p<0.01 compared with A4-7 24 h, and ••p<0.01 between different cell lines at the same time point, **p<0.01 compared with untreated control); and (FIG. 5F) an image and graphs showing the effects of α1 Na/K-ATPase knock-down on tumor growth, where DU-P1 and A4-7 cells were xenografted into NOD/SCID mice and tumor growth was assessed by measuring the tumor volume at different time points, where photos of tumors harvested from xenografted mice are shown in the upper panel, and where quantitative data of tumor weight and volume from xenografted DU-P1 and A4-7 cells are presented in the lower panel (*p<0.05 and p<0.01 compared with basal tumor volume, ##p<0.01 compared between DU-P1 xenograft and A4-7 xenograft at the same time point (Two-way ANOVA), and p<0.01 compared with DU-P1 xenograft weight (Student's T-test)).

(FIG. 6A) images and graphs showing the expression of α1 Na/K-ATPase in prostate cancer, where left panels show α1 expression patterns in paired human normal prostate tissue (left), carcinoma (middle) and bone metastasis (right), where human tissue arrays were immunostained with a α1 monoclonal antibody (in brown), where hematoxylin was used for counterstaining of cell nucleus (in blue), where quantitative data are shown on the right side. p<0.0001 (one-way ANOVA, Bartlett's test), and where down-regulation of α1 Na/K-ATPase in prostate cancer was further verified by paired tissue analysis (right-most panel) p<0.001, paired T-test (Wilcoxon signed-rank test); (FIGS. 6B-6C) images and graphs showing the expression of α1 Na/K-ATPase in breast and kidney cancers, where left panels show α1 Na/K-ATPase expression patterns in normal tissues, cancer and metastatic lesions as in A, and where right panel shows quantitative data of α1 staining (**p<0.0001 (one-way ANOVA, Bartlett's test); (FIG. 6D) a table showing a comparison of α1 Na/K-ATPase expression in three different human cancers, where the quantitative measurements of Na/K-ATPase α1 expression in FIGS. 6A-6A are tabled; and (FIG. 6E) graphs showing transcriptional down-regulation of Na/K-ATPase α1 (ATP1A1) gene expression and kidney cancer patient survival, where the left panel shows a decrease in α1 expression in human kidney cancer (TCGA-KIRC database, n=530), paired T-test (Wilcoxon signed-rank test), and where the right panel shows an inverse correlation between the α1 gene expression and patient survival (log-rank survival test).

(FIG. 8A) a graph showing expression of α1 and α2 CD2 in different cell lines, where different cell lines were generated and cell lysates were prepared and subjected to Western blot using anti-GFP antibody; (FIG. 8B) a schematic diagram showing the amino acid sequence of CD2 (second cytoplasmic domain) of α1 Na/K-ATPase, where the N terminal fragment, denoted as CD2N, is labeled with an initial line and the C terminal fragment, denoted as CD2C, is labeled with a further line, and where the predicted Src binding region is shown in a box; (FIG. 8C) images showing expression of CD2N and CD2C fragment in different cell lines, where YFP-CD2N and YFP-CD2C cell lines were prepared and cell lysates were made from each cell line as indicated, and subjected to Western blot; (FIG. 8D) a graph showing the effects of ouabain on ERK activation, where cells were treated with ouabain as indicated, and cell lysates were made and subjected to Western blot analyses of ERK activation (pERK1/2/ERK 1/2) (*p<0.05 compared with vehicle-treated control of the same cell line, #p<0.05 compared between different cell lines under the same treatment); (FIG. 8E) images showing an in vitro assay illustrating Y260 phosphorylation of purified GST or GST-α1 CD2 (5 μg) by purified recombinant Src or Lyn (4.5 units) in the presence of 2 mM $Mg^{2+}$-AT, where the upper panel shows pY260 α1 blot and the lower panel shows Ponceau-S staining of the same membrane.

(FIG. 9A) expression of rat α1 Na/K-ATPase in different cell lines, where Y260A mutant cell lines were generated and cell lysates from 3 different clones were analyzed for rat α1 Na/K-ATPase using a rat α1-specific antibody (NASE), where porcine LLC-PK1 and rat α1-rescued AAC-19 cells were used as a negative and positive control, and where tubulin was probed as a loading control on the same membrane; (FIG. 9B) α1 and β1 subunit expression in Y260A, where mutant clone 21 was compared with control AAC-19 and α1 knockdown cell line PY-17 using alpha6F antibody that recognizes both porcine and rat α1 (p<0.01 compared with AAC-19 (One-way ANOVA)); (FIG. 9C) immunofluorescence staining showing α1 Na/K-ATPase expression in the plasma membrane of AAC-19 and Y260A mutant clone 21 cells; (FIG. 9D) a $^3H$ ouabain binding study showing endogenous (porcine) α1 Na/K-ATPase expression in Y260A mutant clone 21 as compared with the parental α1 knockdown cell line PY-17 (p<0.01 as compared with PY-17 (Students T test)); (FIG. 9E) a Na/K-ATPase activity assay; (FIG. 9F) a comparison of protein phosphorylation between AAC-19 and Y260A cells, including a Western blot showing Y418 and Y529 phosphorylation of Src kinase, where total Src was also probed as loading control, where quantitative data is shown on right (p<0.01 to AAC-19 cells (Student T-test)) and where total protein tyrosine phosphorylation blots are shown at the bottom; and (FIG. 9G) protein phosphorylation in response to Src inhibition by PP2, where representative blots and quantification of Src activity (pY418) are shown (p<0.01 to control (Student T-test));

(FIG. 10A) total α1 and β1 subunit expression in Y260 mutant clone 24 as compared with control AAC-19; and (FIG. 10B) a Western blot showing ouabain-induced ERK activation (pERK1/2/ERK 1/2) in AAC-19 and Y260A clone 24 cells (**p<0.01 compared with vehicle-treated control (the same cell line), ##p<0.01 compared with different cell lines, ••p<0.01 between different cell lines in the same treatment dose as indicated (Two-way ANOVA)).

FIGS. 11A-11E include graphs, images and a table showing: (FIG. 11A) a comparison of cell proliferation rate of AAC-19 and Y260A cells (*p<0.05 and p<0.01 compared to 0-hour in same cell line and ••p<0.01 compared between two cell lines at the same time point (Two-way ANOVA)); (FIG. 11B) OCAR measurement of AAC-19 and Y260A, where Maximal Respiration and Proton Leak data were generated and calculated from the OCAR measurements, and where Respiratory Control Ratio is calculated based on the equation as shown; (FIG. 11C) Coupling Efficiency as calculated from the OCAR measurements (p<0.01 compared with control AAC-19); (FIG. 11D) RNAseq analyses showing upregulated genes involved in metabolic switch in Y260A mutant cells, as compared with AAC-19, where upregulation is expressed as Log 2 ratio; (FIG. 11E) Y260A cells treated with 5 μM PP2 for overnight and qPCR used to measure mRNA expression level of different genes (**p<0.01 compared with untreated control).

FIGS. 12A-12E include images and graphs showing: (FIG. 12A) co-immunoprecipitation to compare α1 Na/K-

ATPase/Src kinase interaction in normal prostate RWPE1 vs. prostate cancer cell line DU145 (on left) and in normal breast MCF10A vs. breast cancer cell line MDAMB231 (on right); (FIG. 12B) a Western blot showing α1 Na/K-ATPase expression in DU145, DU-P1 (control) and α1-knockdown cell lines (A4-3 and A4-7); (FIG. 12C) EGF stimulation of DU-P1 and A4-7 cells, where cells were exposed to different concentrations of EGF for 5 minutes and Src activation (pY418 Src/c-Src) and EGFR activation at Src-mediated phosphorylation site (pY845 EGFR/EGFR) were measured by Western blot; (FIG. 12D) A4-7 cells treated with 5 μM PP2 for 90 m and lysates from control and treated cells were assayed for the activation of Src, ERK and EGFR, where the same lysates were also probed for Myc expression (**p<0.01 compared with untreated control); and (FIG. 12E) ECAR measurement of A4-7 cells cultured in the presence or absence of PP2 (5 μM, 4 h).

(FIG. 13A) Na/K-ATPase α1 (ATP1A1) gene expression decreased in prostate cancer compared with normal prostate in the TCGA-PRAD database, n=495; and (FIG. 13B) that a decrease in α1 gene expression in the same database based on best cutoff value was not correlated with patient survival.

DESCRIPTION OF EXEMPLARY EMBODIMENTS

Figures 1A, 1B:
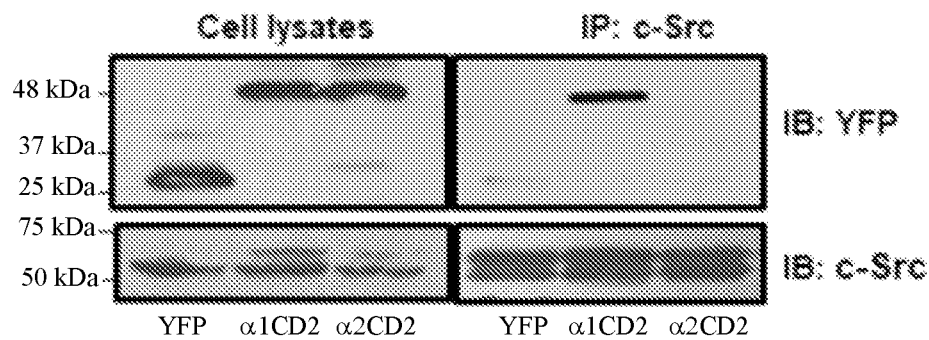
FIGS. 1A-1E include images, tables, and graphs showing the identification of Y260 in $\alpha 1$ Na/K-ATPase as a Src binding site, including.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

It is appreciated that the α1 subunit of Na/K-ATPase binds with Src kinase to form a receptor complex, whose activation/inactivation is regulated in a conformation-dependent manner. Furthermore, in vitro and in vivo studies have indicated that the α1 Na/K-ATPase could regulate Src through a mechanism of two pair of domain interactions. The second cytosolic domain of α1 subunit acts like a Src SH2 ligand, and the nucleotide binding domain of α1 binds the kinase domain and keeps Src in an inactive state. Moreover, although there are four isoforms of the a subunit, only α1 acts as a dynamic regulator of Src kinase, as evident from studies with other isoforms. In this regard, the presently-disclosed subject matter is based, at least in part, on that isoform-specific Src regulation and the identification of the Y260 amino acid residue of the α1 Na/K-ATPase as a Src-interacting site. In particular, it has been determined that Y260 is a Src-specific phosphorylation site and important to the formation of a constitutive functional receptor complex that allows dynamic regulation of Src-mediated signal transduction. Moreover, it has been discovered that disruption of that interaction results in a metabolic switch in cells and is a contributing factor in the reprogramming of metabolism observed in cancer cells, a phenomenon also known as Warburg effect. As described in further detail below, many cancer cells showed reduced expression of α1 Na/K-ATPase and decreased Y260 phosphorylation, and it has now been determined that Y260 in α1 Na/K-ATPase is a Src-specific phosphorylation and binding site, which is required for Na/K-ATPase/Src-mediated signal transduction, and which, in turn, enables a dynamic control of aerobic glycolysis with decreased phosphorylation of Y260 leading to increased cellular aerobic glycolysis and lactate production, while also sensitizing cells to glycolytic inhibition due to a decrease in glycolytic capacity and reserve.

The presently-disclosed subject matter thus includes systems and methods that make use of the Y260 phosphorylation as a biomarker for Na/K-ATPase-mediated Src signaling for the diagnosis and prognosis of cancer. In some embodiments, a method of detecting Na/K-ATPase-mediated Src signaling is provided that comprises the steps of obtaining a biological sample, and determining an amount in the sample of phosphorylation of a Y260 reside in a Na/K-ATPase present in the biological sample. In some embodiments, the Na/K-ATPase is an α1 Na/K-ATPase isoform (see, e.g., Official Symbol/Gene: ATPA1, GEN ID: 476, SWISSPROT ENTRY ID: P05023 (human)).

In some embodiments, a method for diagnosis or prognosis of a cancer in a subject is provided that comprises the steps of: obtaining a biological sample; determining an amount of a phosphorylation of a Y260 residue in a Na/K ATPase present in the biological sample; and comparing the amount of the phosphorylation in the sample, if present, to a control level of the phosphorylation, wherein the subject is diagnosed as having a cancer or a risk thereof if there is a reduction in the amount of the phosphorylation in the sample as compared to the control level. In some embodiments, the presently-disclosed subject matter includes methods and systems for diagnosing cancer a subject, and for determining whether to initiate or continue prophylaxis or treatment of cancer in a subject, by determining an amount of a phosphorylation of a Y260 residue in a Na/K ATPase in a biological sample from a subject. In some embodiments, the Na/K ATPase is an α1 Na/K ATPase isoform.

The terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example an amount of a phosphorylation of a Y260 residue in a Na/K ATPase, the amount (including presence or absence) of which is indicative of the presence, severity, or absence of the condition.

Along with diagnosis, clinical disease prognosis is also an area of great concern and interest. It is important to know the stage and rapidity of advancement of the cancer in order to plan the most effective therapy. If a more accurate prognosis can be made, appropriate therapy, and in some instances less severe therapy for the patient can be chosen. Measurement of phosphorylation levels disclosed herein can be useful in order to categorize subjects according to advancement of the cancer who will benefit from particular therapies and differentiate from other subjects where alternative or additional therapies can be more appropriate.

As such, "making a diagnosis" or "diagnosing", as used herein, is further inclusive of determining a prognosis, which can provide for predicting a clinical outcome (with or without medical treatment), selecting an appropriate treatment (or whether treatment would be effective), or monitoring a current treatment and potentially changing the treatment, based on the measure of diagnostic biomarker levels disclosed herein (e.g., the amount of phosphorylation of a Y260 residue in a Na/K ATPase).

The phrase "determining a prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of test biomarkers. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., not having a reduction in Y260 phosphorylation), the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a Y260 phosphorylation level of less than a control level in some embodiments can signal that a subject is more likely to suffer from a cancer than subjects with a phosphorylation level more than or equal to the control level, as determined by a level of statistical significance. Additionally, a change in phosphorylation levels from baseline levels can be reflective of subject prognosis, and the degree of change in phosphorylation levels can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In other embodiments, a threshold degree of change in the level of a prognostic or diagnostic indicator can be established, and the degree of change in the level of the indicator in a biological sample can simply be compared to the threshold degree of change in the level. A preferred threshold change in the level for Y260 phosphorylation described herein is about 5%, about 10%, about 15%, about 20%, about 25%, about 30%, about 50%, about 75%, about 100%, and about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments of the presently-disclosed subject matter, multiple determination of one or more diagnostic or prognostic indicators can be made, and a temporal change in the amount of Y260 phosphorylation in a Na/K ATPase can be used to monitor the progression of disease and/or efficacy of appropriate therapies directed against the disease. In such an embodiment, for example, one might expect to see an increase in the Y260 phosphorylation in a Na/K ATPase over time during the course of effective therapy. Thus, the presently-disclosed subject matter provides in some embodiments a method for determining treatment efficacy and/or progression of a cancer in a subject. In some embodiments, the method comprises determining an amount of Y260 phosphorylation in a Na/K ATPase in biological samples collected from the subject at a plurality of different time points and comparing the amounts of the Y260 phosphorylation in the Na/K ATPase in the samples collected at different time points. For example, a first time point can be selected prior to initiation of a treatment and a second time point can be selected at some time after initiation of the treatment. One or more Y260 phosphorylation levels can then be measured in each of the samples taken from different time points and qualitative and/or quantitative differences noted. A change in the amounts of the biomarker levels from the first and second samples can be correlated with determining treatment efficacy and/or progression of the disease in the subject.

The terms "correlated" and "correlating," as used herein in reference to the use of diagnostic and prognostic biomarkers, refers to comparing the presence or quantity of the biomarkers in a subject to its presence or quantity in subjects known to suffer from, or known to be at risk of, a given condition (e.g., a cancer); or in subjects known to be free of a given condition, i.e. "normal individuals". For example, a Y260 phosphorylation level in a biological sample can be compared to a level known to be associated with a specific type of cancer. The sample's Y260 phosphorylation level is said to have been correlated with a diagnosis; that is, the skilled artisan can use the phosphorylation level to determine whether the subject suffers from a specific type of cancer, and respond accordingly. Alternatively, the sample's Y260 phosphorylation level can be compared to a control marker level known to be associated with a good outcome (e.g., the absence of a cancer), such as an average level found in a population of normal subjects.

In certain embodiments, a diagnostic or prognostic biomarker is correlated to a condition or disease by merely its presence or absence. In other embodiments, a threshold level of a diagnostic or prognostic Y260 phosphorylation can be established, and the level of the Y260 phosphorylation in a subject sample can simply be compared to the threshold level.

As noted, in some embodiments, multiple determination of one or more diagnostic or prognostic biomarkers can be made, and a temporal change in the marker can be used to determine a diagnosis or prognosis. For example, a diagnostic level of phosphorylation can be determined at an initial time, and again at a second time. In such embodiments, a decrease in the Y260 phosphorylation from the initial time to the second time can be diagnostic of a particular type of cancer or a given prognosis. Furthermore, the degree of change of one or more markers can be related to the severity of cancer and future adverse events, including metastasis, as described further herein below.

The skilled artisan will understand that, while in certain embodiments comparative measurements can be made of the same diagnostic marker at multiple time points, one can also measure a given marker at one time point, and a second marker at a second time point, and a comparison of these markers can provide diagnostic information.

With regard to the step of providing a biological sample from the subject, the term "biological sample" as used herein refers to any body fluid or tissue potentially comprising a Na/K-ATPase. In some embodiments, for example, the biological sample can be a blood sample, a serum sample, a plasma sample, or sub-fractions thereof. In some embodiments, the biological sample comprises one or more cells, such as cancer cells obtained from a tumor biopsy or other source. In some embodiments, in view of the disruption of Src and the Na/K-ATPase as a contributing factor in the reprogramming of metabolism observed in cancer cells, the methods of the presently-disclosed subject matter can further include a step of selecting or modifying a treatment for a cancer based on the determined amount of phosphorylation of the Y260 residue in the subject. In some embodiments, a chemotherapeutic or other anti-cancer agent can then be administered to the subject subsequent to diagnosing the subject as having a cancer or a risk thereof. In some embodiments, an amount of Src activity can also be measured in the biological sample as an additional diagnostic or therapeutic indicator.

Turning now to the step of identifying an amount of Y260 phosphorylation in a Na/K-ATPase or Src activity present in the biological sample, various methods known to those skilled in the art can be used to identify such phosphorylation and activity in the provided biological sample. In some embodiments, determining the amount of biomarkers in samples comprises the use of mass spectrometry and/or immunoassay devices and methods to measure Y260 phosphorylation in samples, although other methods are well known to those skilled in the art as well. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

In some embodiments of the presently-disclosed subject matter, Y260 phosphorylation can be determined by making use of antibodies specific for phosphorylated Na/K-ATPase isoforms, such as the α1 isoform. In other embodiments, Y260 phosphorylation can be determined by co-immunoprecipitating Src and Na/K-ATPase. In some embodiments, given the requirement of Y260 phosphorylation for Na/K-ATPase-mediated Src signaling, Y260 phosphorylation is determined by assessing activation of protein kinases known to be downstream of Src, including, but not limited to, ERK and Akt.

In some embodiments, mass spectrometry (MS) analysis can be used alone or in combination with other methods (e.g., immunoassays) to determine the presence and/or quantity of the Y260 phosphorylation in a Na/K-ATPase in a biological sample. In some embodiments, the MS analysis comprises matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers, such as for example triple quadrupole mass spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated herein by this reference.

Although certain embodiments of the method only call for a qualitative assessment of the presence or absence of Y260 phosphorylation of a Na/K-ATPase in the biological sample, other embodiments of the method call for a quantitative assessment of the amount of Y260 phosphorylation of a Na/K-ATPase in the biological sample. Such quantitative assessments can be made, for example, using one of the above mentioned methods, as will be understood by those skilled in the art.

In certain embodiments of the presently-described methods, it can be desirable to include a control sample that is analyzed concurrently with the biological sample, such that the results obtained from the biological sample can be compared to the results obtained from the control sample. Additionally, it is contemplated that standard curves can be provided, with which assay results for the biological sample can be compared. Such standard curves present levels of phosphorylation as a function of assay units, i.e., fluorescent signal intensity, if a fluorescent signal is used. Using samples taken from multiple donors, standard curves can be provided for control levels of the one or more markers in normal tissue.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker levels over time. Increases or decreases in marker levels, as well as the absence of change in marker levels, can provide useful information about the disease status that includes, but is not limited to identifying the approximate time from onset of the event, the presence and amount of salvageable tissue, the appropriateness of drug therapies, the effectiveness of various therapies, and identification of the subject's outcome, including risk of future events.

The analysis of markers can be carried out in a variety of physical formats as well. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

As mentioned above, depending on the embodiment of the method, identification of the amount of Y260 phosphorylation or other markers can be a qualitative determination of the presence or absence of the markers, or it can be a quantitative determination of the concentration of the markers. In this regard, in some embodiments, the step of identifying the subject as having cancer or a risk thereof requires that certain threshold measurements are made, i.e., the levels of the Y260 phosphorylation in the Na/K-ATPase in the biological sample are below a control level. In certain embodiments of the method, the control level is any detectable level of the Y260 phosphorylation in the Na/K-ATPase or other markers. In other embodiments of the method where a control sample is tested concurrently with the biological sample, the control level is the level of detection in the control sample. In other embodiments of the method, the control level is based upon and/or identified by a standard curve. In other embodiments of the method, the control level is a specifically identified concentration, or concentration range. As such, the control level can be chosen, within acceptable limits that will be apparent to those skilled in the art, based in part on the embodiment of the method being practiced and the desired specificity, etc.

With respect to the cancer diagnosed in accordance with the presently-disclosed subject matter, the term "cancer" is used herein to refer to all types of cancer or neoplasm or malignant tumors found in animals, including leukemias, carcinomas, melanoma, and sarcomas. Examples of cancers are cancer of the brain, bladder, breast, cervix, colon, head and neck, kidney, lung, non-small cell lung, mesothelioma, ovary, prostate, sarcoma, stomach, uterus and Medulloblastoma. In some embodiments, the cancer is selected from the group consisting of prostate cancer, kidney cancer, and breast cancer. In some embodiments, the cancer is a metastatic cancer.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer. In some embodiments, the cancer is selected from prostate cancer and/or breast cancer.

Further provided, in some embodiments of the presently-disclosed subject matter are methods and assays for detecting a metabolic switch from oxidative phosphorylation to aerobic glycolysis. In some embodiments, such detection methods include steps of: obtaining a biological sample including one or more cells; and determining an amount of a phosphorylation at a Y260 residue in a Na/K ATPase present in the one or more cells. In some embodiments, the detection methods further include a step of determining an amount of lactate produced in the one or more cells. In some embodiments, the Na/K ATPase is an α1 Na/K ATPase isoform. In some embodiments, the one or more cells comprises a cancer cell, such as, in certain embodiments, a prostate cancer cell, a kidney cancer cell, or a breast cancer cell.

In some embodiments of the presently-disclosed subject matter, a system or assay for detecting Na/K-ATPase-mediated Src signaling and/or for determining an amount of a phosphorylation at a Y260 residue in a Na/K ATPase is provided. Such systems and assays can be provided, for example, as commercial kits that can be used to test a biological sample, or series of biological samples, from a subject. The system can also include certain samples for use as controls. The system can further include one or more standard curves providing levels of markers as a function of assay units.

In some embodiments, a system or assay for the analysis of biomarkers is provided that comprises antibodies having specificity for Y260 phosphorylation in a Na/K-ATPase. Such a system or assay can comprise devices and reagents for the analysis of at least one test sample. The system can further comprise instructions for using the system and conducting the analysis on a sample obtained from a subject.

With respect to the presently-disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials and Methods

Antibodies and their sources. Monoclonal anti-Src antibody (B12), polyclonal anti-ERK1/2 (Extracellular Regulatory Kinase 1/2) antibody, monoclonal anti-phospho ERK1/2 antibody, goat anti-mouse IgG HRP and goat anti-rabbit IgG HRP secondary antibodies—Santa Cruz Biotechnology (Santa Cruz, Calif.). Anti-Src (Y418) rabbit polyclonal antibody—Invitrogen (Carlsbad, Calif.). Anti-Akt, anti-phospho-Akt (S473), anti-PKM2 and anti-phospho-PKM2 (Y105) rabbit antibodies, phosphoFAK576/7 and FAK rabbit antibodies—Cell Signaling Technologies (Danver, Mass.). Monoclonal anti-α1 Na/K-ATPase subunit antibody (α6f)—Developmental Studies Hybridoma Bank at The University of Iowa (Iowa City, Iowa). Monoclonal anti-Src (GD-11) antibody, polyclonal rabbit anti-α1 Na/K-ATPase (06-520), Protein-G-agarose beads for immunoprecipitation and PP2-Millipore (Billerica, Mass.). Anti-GFP and anti-c-Myc rabbit polyclonal antibodies—Abcam (Cambridge, Mass.). Anti-phospho-α1 Na/K-ATPase (Y260)-Assay Biotech (Fremont, Calif.). Transfection kit (Lipofectamine 2000) was from Invitrogen. QuikChange mutagenesis kit was from Stratagene (La Jolla, Calif.). Polyclonal rat α1 specific-antibody (anti-NASE) was kindly gifted by Dr. Thomas Pressley (Texas Tech University, Lubbock, Tex.). All other reagents were purchased from Sigma-Aldrich (St. Louis, Mo.).

Mice studies. Animal protocols were approved by the Institutional Animal Care and Use Committee (IACUC) of Marshall University according to NIH guidelines. Male C57/BL6J mice (8-10 weeks old) were humanely sacrificed and different organs were frozen immediately for preparation of tissue lysates for immunoblots. Tumor xenografts were established by subcutaneous injection of $5\times10^6$ DU-P1 or A4-7 cells into the left and right flanks of 6-week-old female NOD/SCID mice (Charles River). Tumor length (L) and width (W) were measured with calipers and tumor volume was estimated as $V=(L\times W^2)/2$.

Immunohistochemical (IHC) Staining Analysis of Human Samples. Na/K-ATPase α1 IHC staining was performed by US Biomax (Rockville, Md.) using human kidney, prostate and breast tissue microarray, and was carried out as described before. As such, it was not possible to record the details of the patients. Antibody for IHC-mouse monoclonal anti-Na/K-ATPase α1 antibody (Millipore). Nucleus was counterstained with hematoxylin. Two independent investigators examined the staining intensity and scored each slide three times as defined: 0, absent; 1, weak; 2, moderate; 3, strong. A mean score was recorded.

Cell culture and cell line generation. All cell lines were purchased from and maintained according to ATCC (Manassas, Va.). LLC-PK1 was serum starved before being used for signaling experiments. AAC-19, Y260A and DU145, A4-7 cell lines were cultured in the presence of 0.5% and 1% serum respectively for 24 hours before being used for the signaling experiments. LLC-PK1 cells were transfected (Lipofectamine 2000) with pEYFP-C1 vector containing α1 CD2, α2 CD2 or pEYFP-C1 empty vector. After verifying YFP expression visually, the cells were selected with 1 mg/ml G418 for one week. G418 resistant clones were selected and expanded. Cells were then cultured without G418 for at least three generations before being used for experiments. CD2N and CD2C cells were generated in similar manner. Y260A cells were generated by transfecting PY-17 cells with pRC/CMV-α1 AACm1 vector harboring mutation at Y260 and selected with ouabain (3 μM). Ouabain-resistant clones were isolated and expanded into stable cell lines. The cells were cultured for at least 3 generations without ouabain before being used for any experiment. DU-P1, A4-7 and A4-3 cell lines were generated by transfecting DU145 cells with a α1 Na/K-ATPase-specific siRNA containing vector and selecting with Puromycin as described above. All constructs were verified by DNA sequencing.

Immunoblot, Immunoprecipitation and Immunostaining Analysis. Immunoblot assays were performed as described previously. Intensity of bands were quantified with ImageJ software (NIH). Immunoprecipitation was performed by adding 5 μg of anti-Src (Millipore Cat #05-184) antibody to 500 μg of cell lysate (1 μg/μl concentration) or 8 μg of anti-α1 Na/K-ATPase antibody (Millipore Cat #06-520) to 800 μg of cell lysate (1 μg/μl concentration). Precipitated proteins were then analyzed as described previously. For immunostaining antibodies used—anti-α1 Na/K-ATPase antibody (Millipore Cat #05-369) and Alexa Fluor 488-conjugated anti-mouse secondary antibody.

Cell growth assay and MTT assay. Cell growth assay and MTT assay were performed as previously described.

Biochemical measurement of ATP and lactate. ATP measurements were performed using CellTiter-Glo Luminescent Cell Viability Assay kit. 10,000 cells per well were cultured in 96-well culture plate. After treatment with 2-DG at indicated concentrations in serum-free DMEM for 45 minutes, assay reagents were reconstituted and added into culture plate. Luminescent counts of the reactants were determined from an opaque-walled 96-well plate with a microplate reader. Lactate measurement was done by colorimetric methods as described by previously. In PP2 study, culture medium containing serum and 5 µM PP2 was replaced in culture dish and collected after 4 hours for measurements.

Bioenergetics. Properties of cellular bioenergetics were characterized using Seahorse XFp Extracellular Flux Analyzer by measuring oxygen consumption rate (OCR) and extracellular acidification rate (ECAR) following the guidelines provided by the manufacturer. Prior to the start of Seahorse assay, optimal FCCP concentration for each cell line was determined by titration studies. Unless indicated otherwise, 10,000 cells per well were seeded with culture medium. Bicarbonate-free medium (Agilent Technologies) with different substrates (10 mM glucose, 2 mM glutamine and 1 mM pyruvate for Cell Mito Stress Test assays; 2 mM glutamine for Glycolysis Stress Test assays) was replaced one hour prior to the assay. Baseline OCR and ECAR rates were measured three times before various inhibitors, stimulants, substrates, or compounds were added through the drug delivery ports. In the PP2 study, cells were pretreated with 5 µM PP2 for 4 h and then analyzed.

$^3$H ouabain binding assay and ATPase Activity Assay. $^3$H-Ouabain Binding Assay and ATPase Activity Assay were performed as previously described.

Cell-attachment induced integrin signaling. Cell-attachment induced integrin signaling were done as previously described.

RNAseq Analysis. RNAseq analysis was performed by BGI Tech, China. Briefly, RNA was extracted from cell lysates, treated with DNase 1 and magnetic Oligod(T) beads were used to isolate mRNA. mRNAs were then fragmented with fragmentation buffer and cDNAs were synthesized using them as templates. After agarose gel electrophoresis, suitable fragments were selected for PCR amplification as templates. During QC steps, Agilent 2100 Bioanalyzer and ABI StepOnePlus Real-Time PCR System were used for quantification and qualification of the sample library. The library was sequenced using HiSeq™ 2000 sequencer. Bioinformatic analysis was performed by deep analysis of gene expression.

RNA Extraction, cDNA Synthesis and Quantitative PCR. Total RNA was isolated with the QIAGEN RNeasy Mini Kit. The same amount of total RNA was used for synthesizing first-stand cDNA with the SuperScript III First-Stand Synthesis SuperMix for qRT-PCR (ThermoFisher). The cDNA from each sample was used as a template for the quantitative PCR (Syber green) with Roche LightCycler® 480 Real-Time PCR System. All primers were synthesized by Integrated DNA Technologies (IDT). β-actin was used as internal control.

Statistical Analysis. Data were recorded as mean +/−SEM (Standard Error of Mean). Student's T-test were used to measure differences between two individual groups and one-way analysis of variance (ANOVA) was used to measure differences between more than two groups. Two-way ANOVA was used to measure between more than two groups while each group contained more than one variables. One-way ANOVA (Bartlett's test) or paired T-test were used to measure differences in the tissue array data, where appropriate. Paired T-test followed by Wilcoxon signed rank test were used to analyze gene expression data from TCGA database. Survival analysis was measured by log-rank survival test. p value less than 0.05 was considered as significant.

Example 1

Identification of Phosphorylated Y260 as a Src-Specific Binding Site

It has been observed that the second cytosolic domain (CD2) of α1 Na/K-ATPase functions like a Src SH2 domain ligand. By comparing amino acid sequences of CD2 from different α isoforms, it was found that α1 CD2, but not CD2 from other isoforms, contain a single Tyr (Y260) residue (FIG. 1A). Because SH2 domains preferentially bind phosphorylated tyrosine containing sequences, it was believed that Y260 might permit the α1 isoform-specific interaction with Src kinase.

Figure 1C:
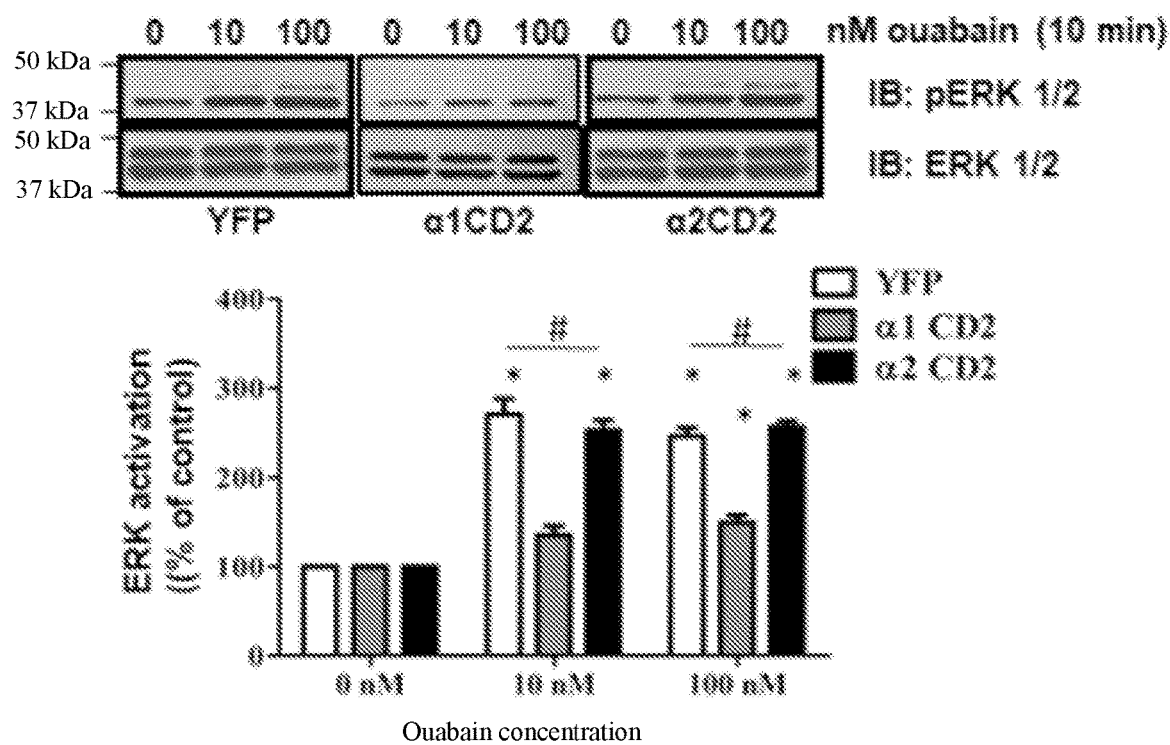
Figure 8A:
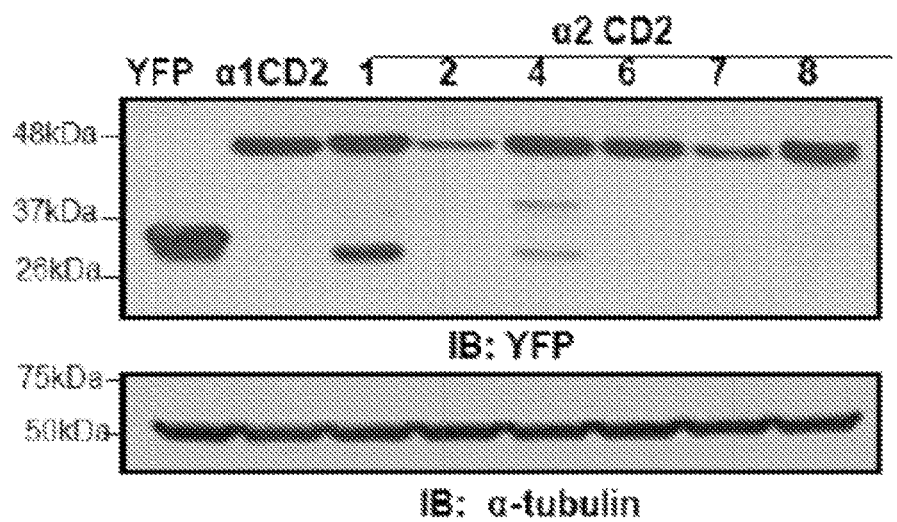
FIGS. 8A-8E include images, schematic diagrams, and graphs, including.
Figure 8B:
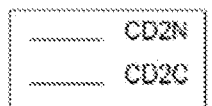
Figure 8C:
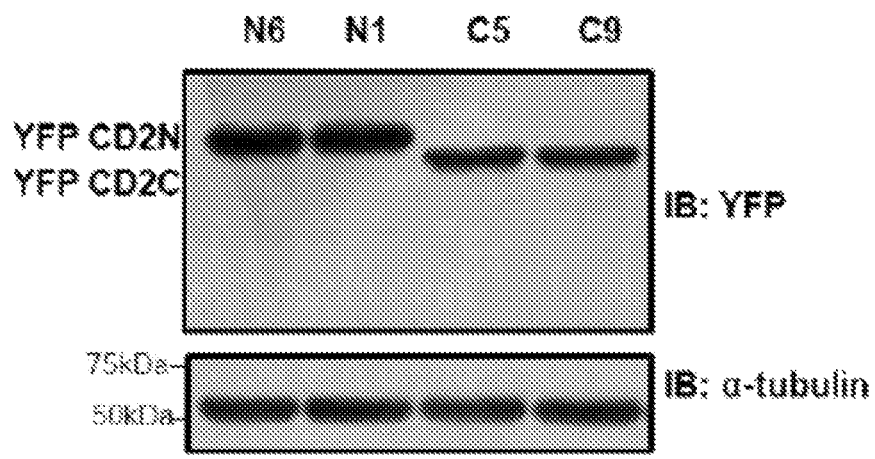
Figure 8D:
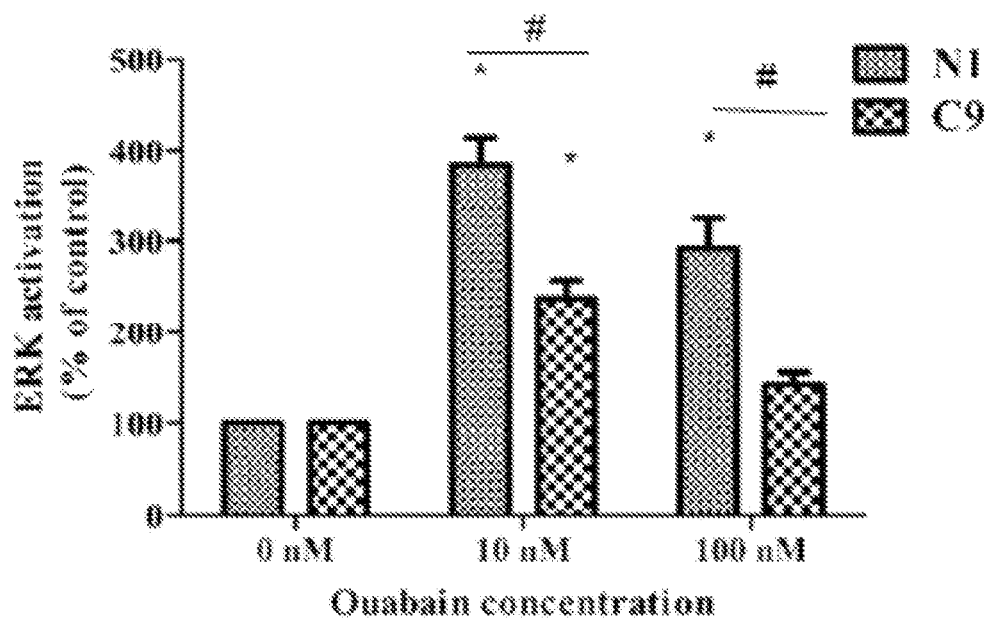

To test this hypothesis, stable cell lines expressing either YFP-α2 CD2 or YFP-α1 CD2 were generated, and their ability to bind and to change Src-mediated signal transduction was then compared (FIG. 8A). As shown in FIG. 1B, α1 CD2, but not α2 CD2 or control YFP, co-immunoprecipitated Src kinase from cell lysate. Consistent with previous findings, the expression of α1 CD2 blocked ouabain-induced ERK activation, whereas α2 CD2 failed to do the same (FIG. 1C). To seek further evidence that Y260 offers isoform-specific interaction with Src, cell lines expressing the N-terminus or C-terminus of α1 CD2 were generated, and demonstrated that the expression of a Y260 containing C-terminal half, but not the N-terminal half, was sufficient to block ouabain-induced ERK activation in cells (FIG. 8B-8D). These results indicated that Y260 could be a Src-specific interaction site present in α1 Na/K-ATPase, but absent in other isoforms.

Figure 1D:
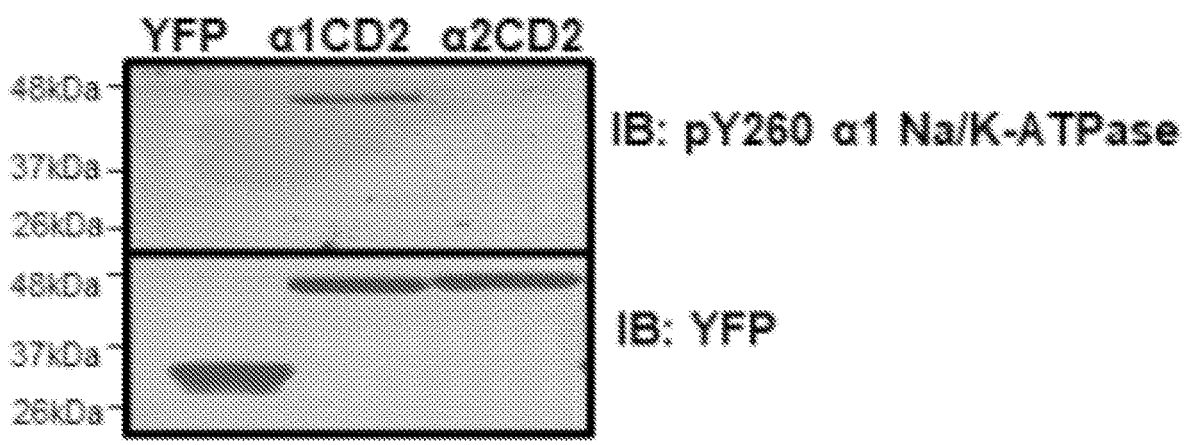
Figure 1E:
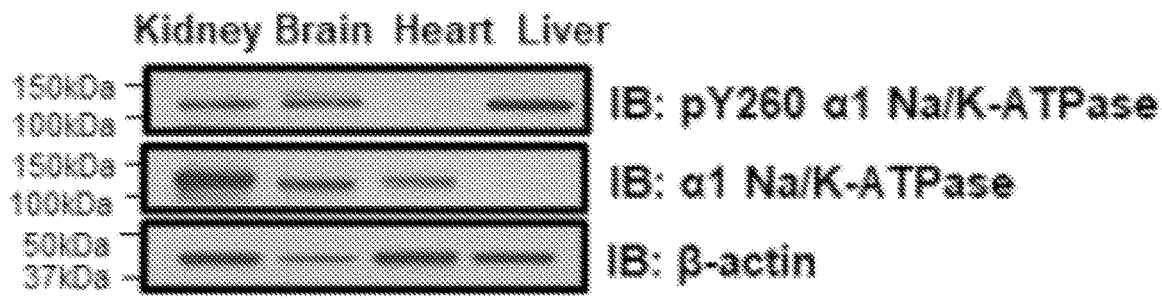

In order to further assess the importance of Y260, it was next determined whether Y260 could be phosphorylated in a Src-dependent manner. In the first set of experiments, α1 CD2 was phosphorylated at Y260 and detected using an anti-pY260 Na/K-ATPase α1 antibody (FIG. 1D). As expected, no phosphorylation was observed in α2 CD2 or control YFP cell lysates. Second, full length α1 Na/K-ATPase was found to be phosphorylated at Y260 in lysates made from mouse tissues including kidney, liver, brain and heart (FIG. 1E). Interestingly, the level of pY260 varied among different tissues with the lowest being expressed in the heart, and the highest in the liver where the total expression of α1 Na/K-ATPase is the lowest among the examined tissues.

Figure 2A:
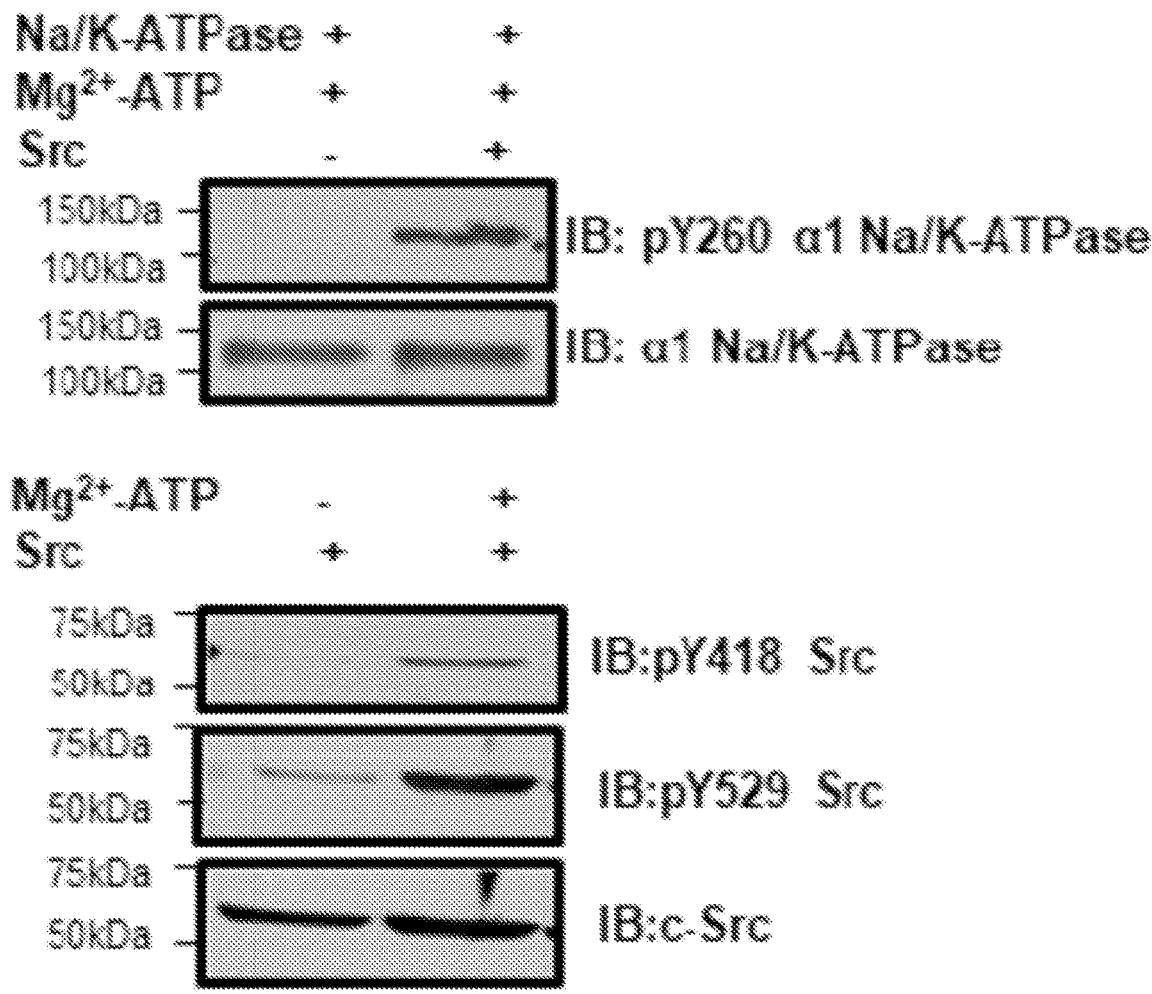
FIGS. 2A-2H include images and graphs showing Y260 phosphorylation and Src, including.
Figure 2B:
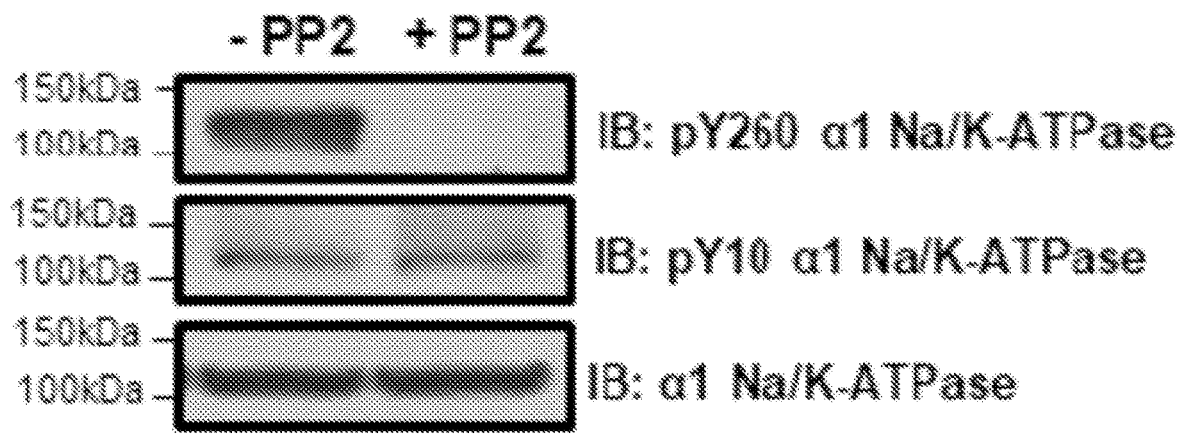
Figure 2C:
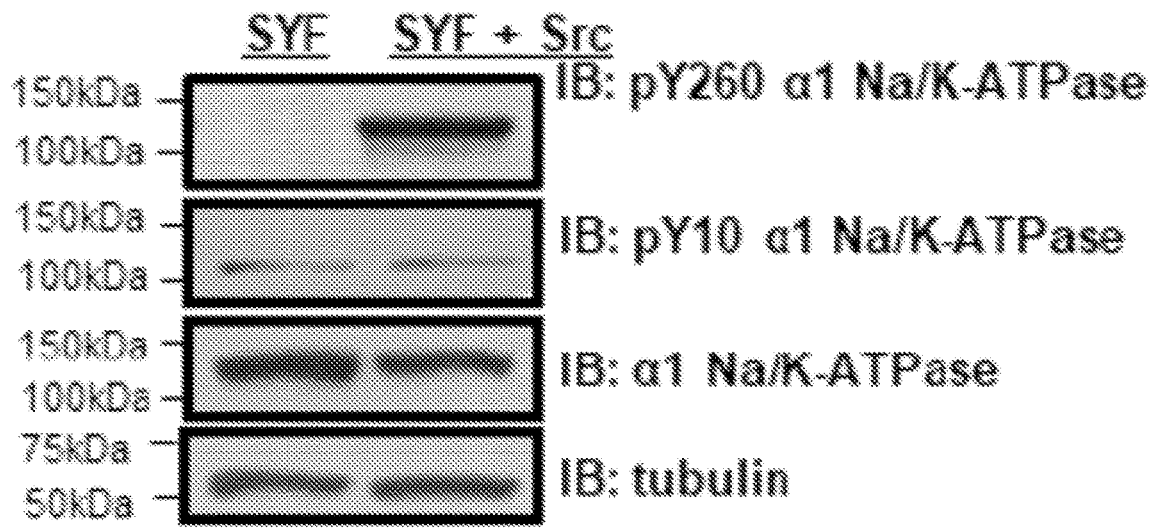
Figure 8E:
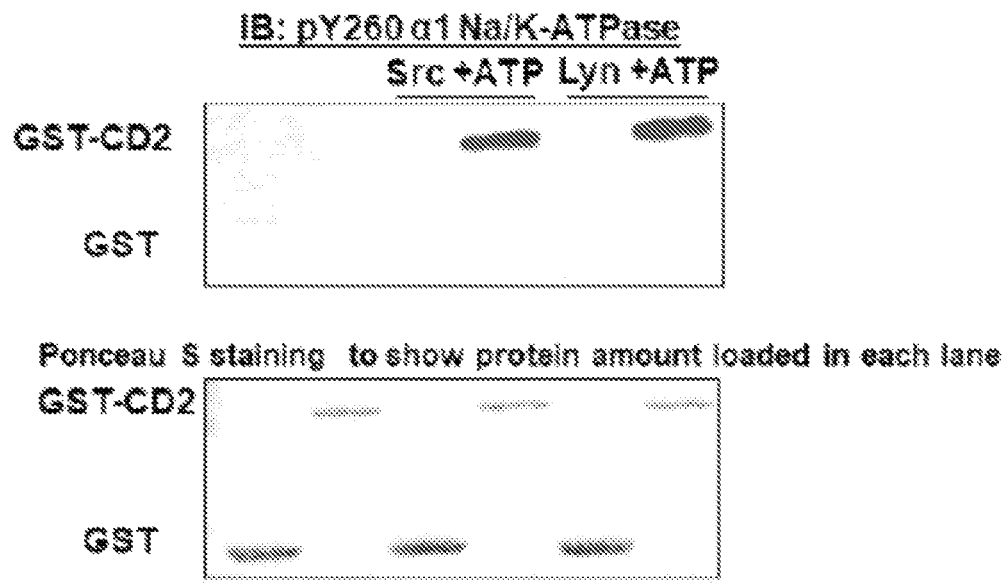

To identify the protein responsible for this phosphorylation, GST tagged α1 CD2 was incubated with purified Src in the presence of ATP, and probed for Y260 phosphorylation using the same anti-pY260 antibody. As depicted in FIG. 8E, phosphorylation was detected in GST-CD2 but not GST. Similarly, Src was able to phosphorylate purified pig kidney α1 Na/K-ATPase at Y260 using an in vitro assay (FIG. 2A). Finally, pretreatment of LLC-PK1 cells with PP2, a Src family kinase inhibitor, attenuated Y260 phosphorylation (FIG. 2B). To further verify the findings, cell lysates were collected from SYF cells, where Src family kinases (Src, Yes and Fyn) are knocked out, and Src-rescued SYF cells (Klinghoffer et al. 1999) As depicted in FIG. 2C, Y260 phosphorylation of α1 Na/K-ATPase was detected in Src-rescued, but not parent SYF cells. The expression of α1 Na/K-ATPase in SYF cells was actually much higher than that in Src-rescued SYF cells. To address the specificity of this regulation, Y10 phosphorylation was also measured in α1 Na/K-ATPase that was mediated by insulin signaling (Feraille et al. 1999). As shown in FIGS. 2B-2C, Y10 phosphorylation was independent of Src kinase. Neither inhibitor nor knockout of Src kinase affected Y10 phosphorylation. These data indicated that Y260 is a Src-specific phosphorylation site and that the anti-pY260 antibody specifically recognizes both truncated and full length α1 Na/K-ATPase polypeptide when they are phosphorylated at Y260.

Example 2

Y260 Phosphorylation Represents a General Feature of Src Signaling

Figure 2D:
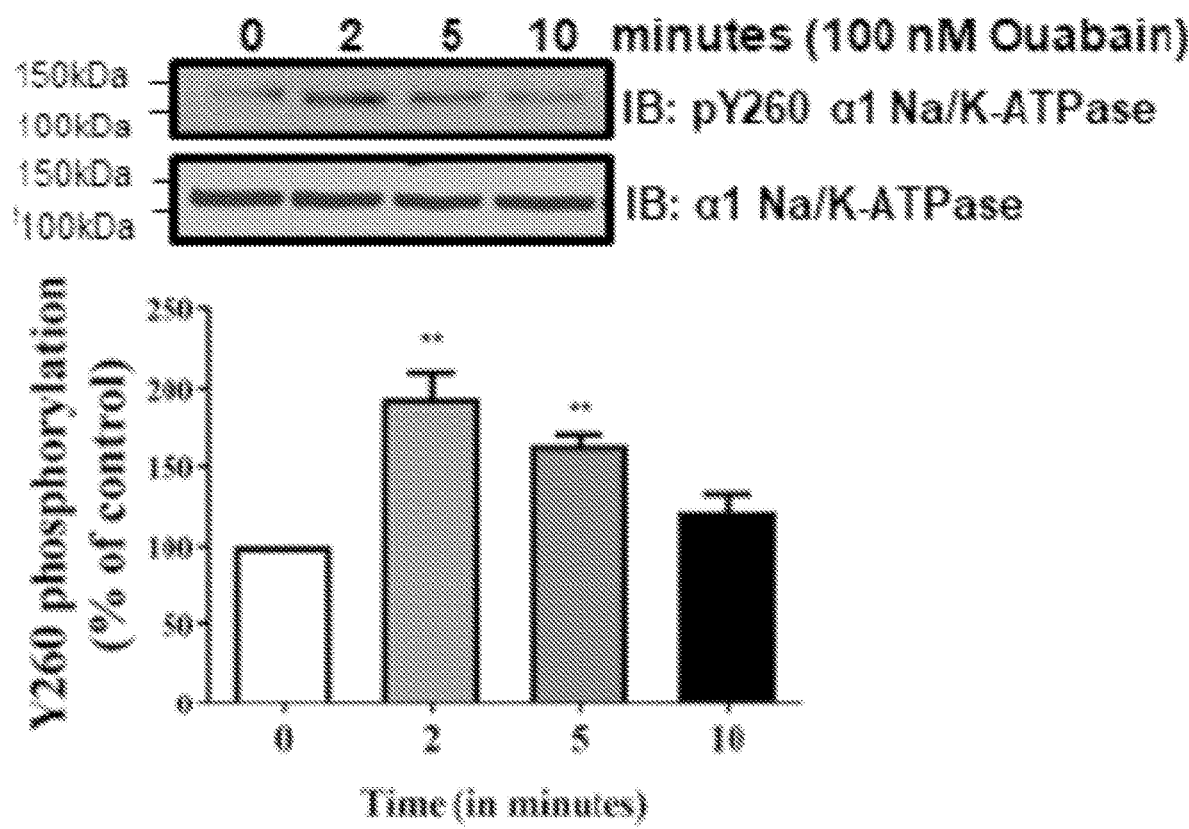
Figure 2E:
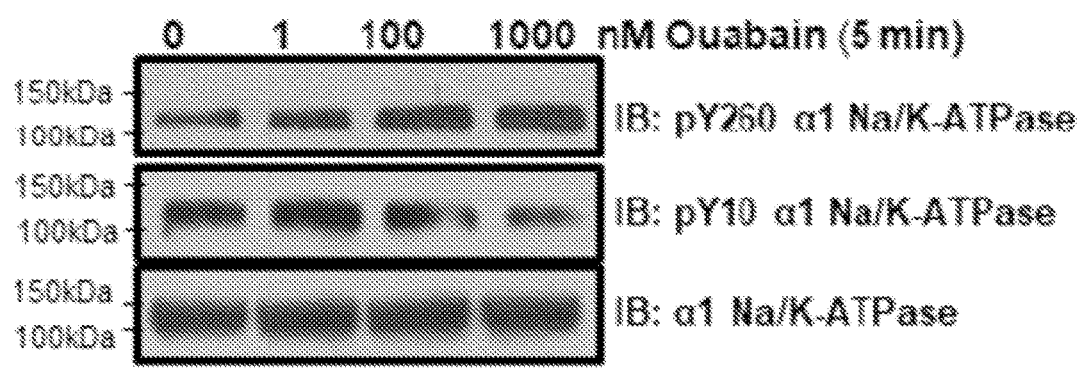
Figure 2F:
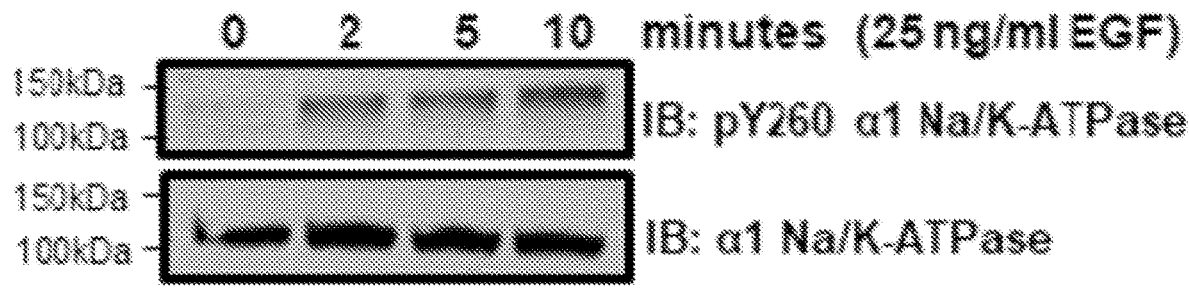
Figure 2G:
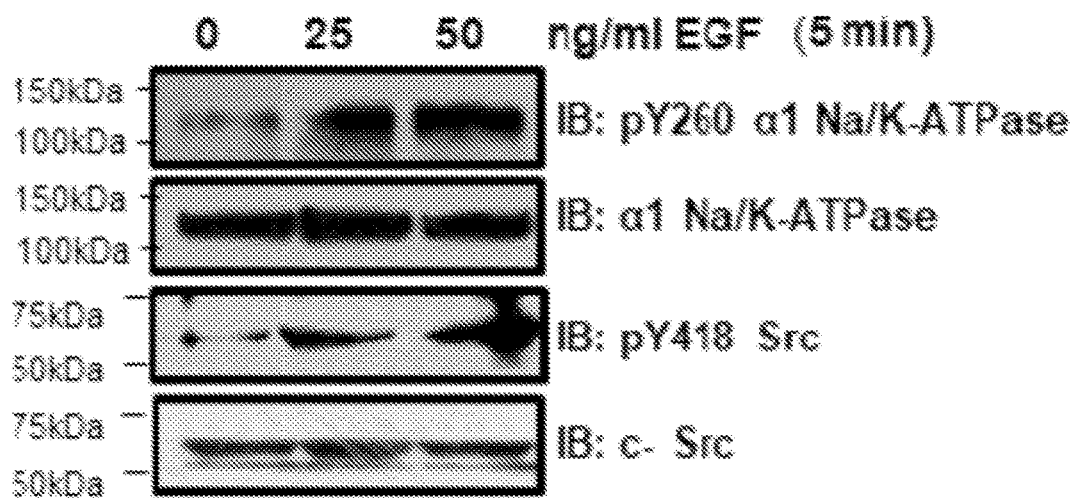
Figure 2H:
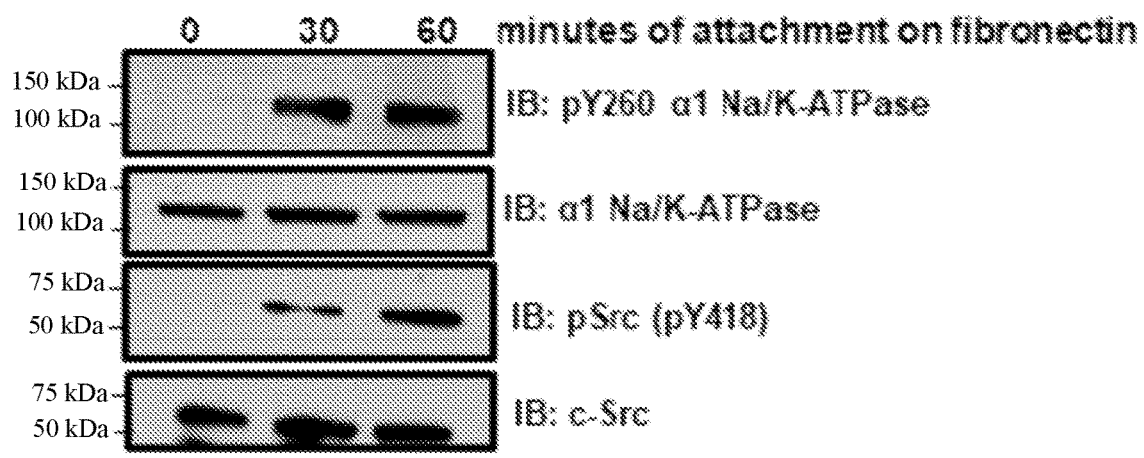

If α1 Na/K-ATPase represents an important general regulator of Src, an increase in Y260 phosphorylation would be expected when cells are stimulated not only by ouabain but also other receptor ligands. Y260 phosphorylation was therefore tested in three different signaling pathways where Src is necessary for signal transduction. First, ouabain increased Y260 phosphorylation in both time and concentration-dependent manner in LLC-PK1 cells (FIGS. 2D-2E). To ensure that that effect was Y260-specific, Y10 phosphorylation was also probed. Consistent with a previous study, ouabain showed no effect on Y10 phosphorylation (FIG. 2E). Second, Y260 phosphorylation was stimulated by EGF. EGF, like ouabain, produced a time- and dose-dependent stimulation of Y260 phosphorylation of Na/K-ATPase as well as Src at Y418 (FIGS. 2F-2G). Furthermore, cells were plated onto fibronectin-coated plates and the stimulation of Y260 phosphorylation was analyzed in the integrin signaling pathway. An increase in Y260 phosphorylation was noted and correlated well with the activation of Src (FIG. 2H). These data indicated that Y260 phosphorylation represented a general feature of Src regulation, not only relevant to receptor function of Na/K-ATPase but also to receptor tyrosine kinases and integrin signaling.

Example 3

Y260 is Required for Na/K-ATPase Mediated Signaling

Figure 9A:
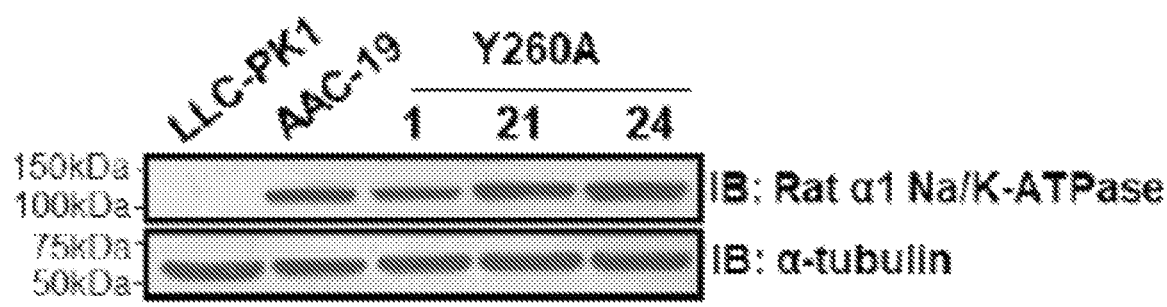
FIGS. 9A-9G includes graphs and images showing.
Figure 9B:
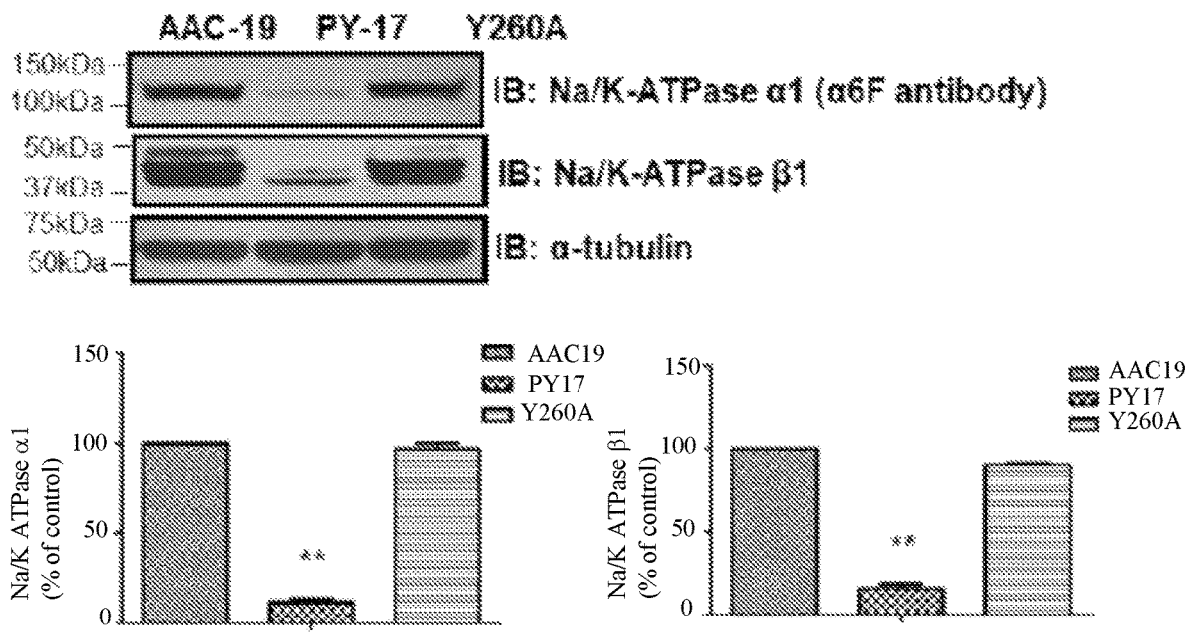
Figure 9C:
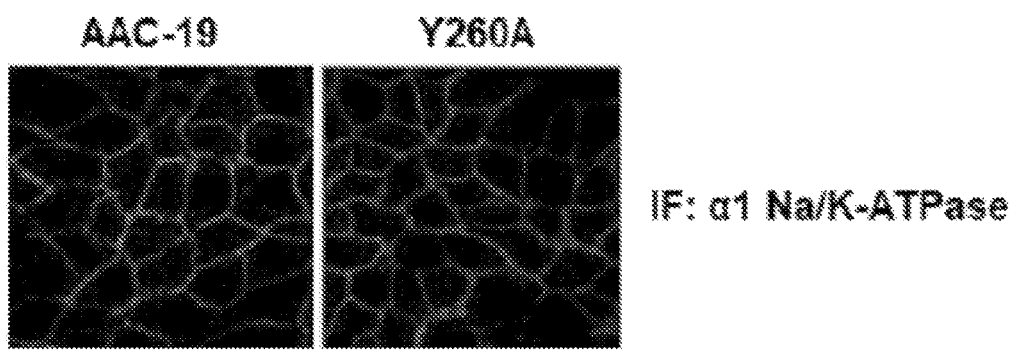
Figure 9D:
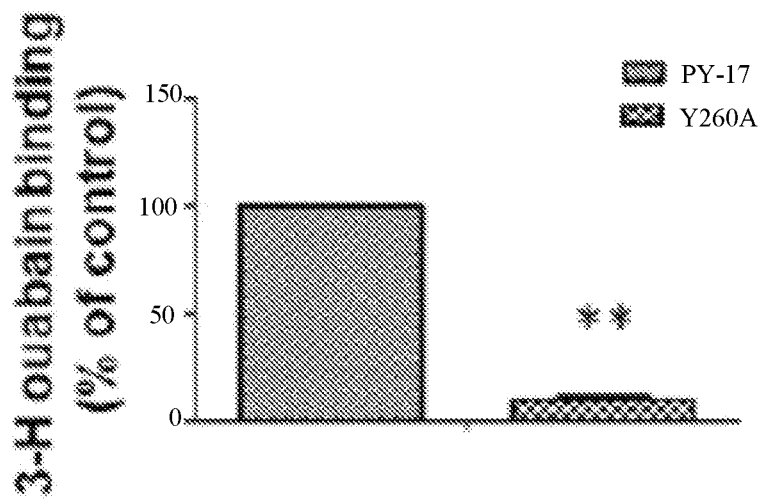
Figure 9E:
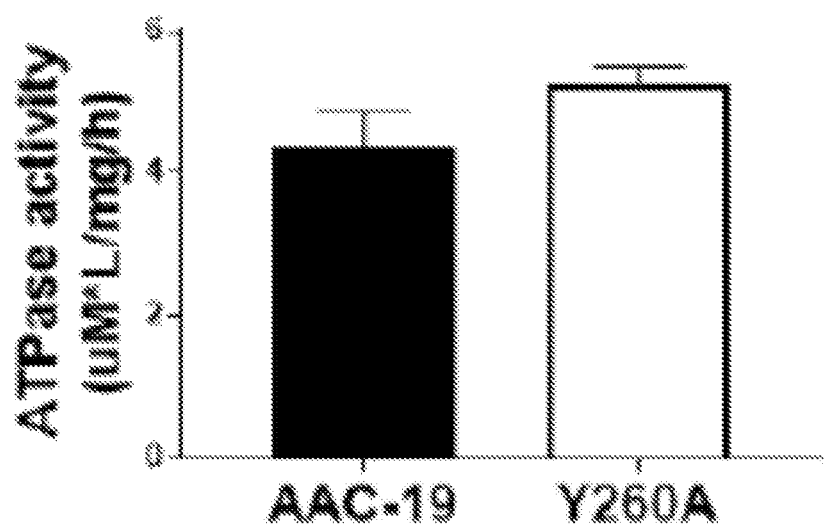

To investigate the role of Y260 in Src-mediated signal transduction, a stable cell line was generated that expresses a loss of function (Y260A) mutant rat α1 Na/K-ATPase. An α1 Na/K-ATPase knockdown cell line, PY-17, was used for transfection. A normal rat α1 Na/K-ATPase-rescued cell line, AAC-19, was used as a control. Control experiments (FIG. 9A) showed that the clone 21 and AAC-19 expressed comparable amount of rat α1. $^3$H-ouabain binding assays indicated that the expression of endogenous pig α1 Na/K-ATPase in Y260A mutant cells only amounted to about 1% of the total Na/K-ATPase (FIG. 9D). Functionally, the expressed Y260A mutant was expressed in the plasma membrane, fully capable of rescuing the expression of β1 subunit and forming a functional Na/K-ATPase exhibiting comparable ouabain-sensitive ATPase activity as in AAC-19 cells (FIGS. 9B-9E).

Figure 3A:
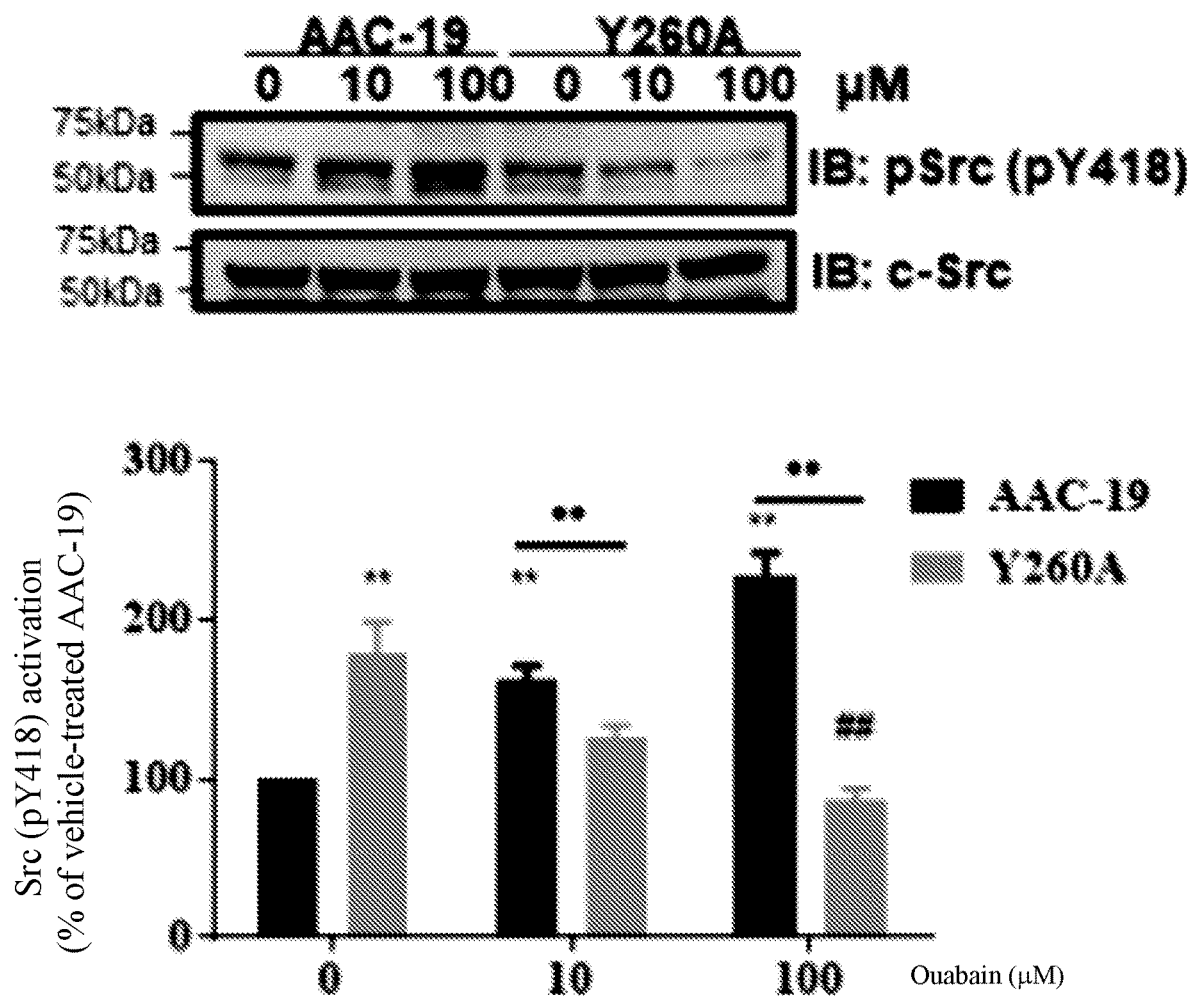
FIGS. 3A-3E include images and graphs showing the effects of Y260A mutation on Src-mediated signal transduction, including.
Figure 3B:
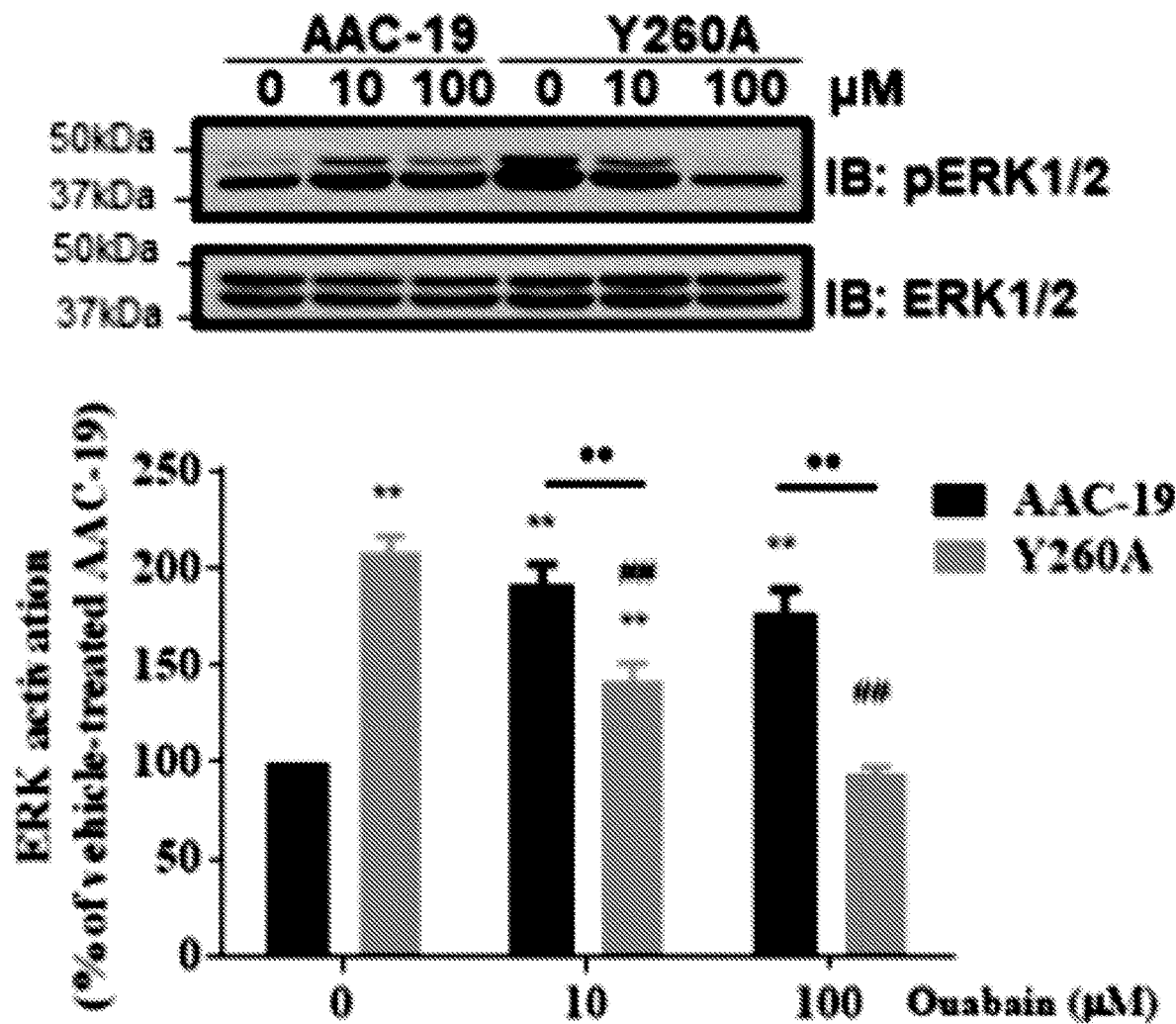
Figure 3C:
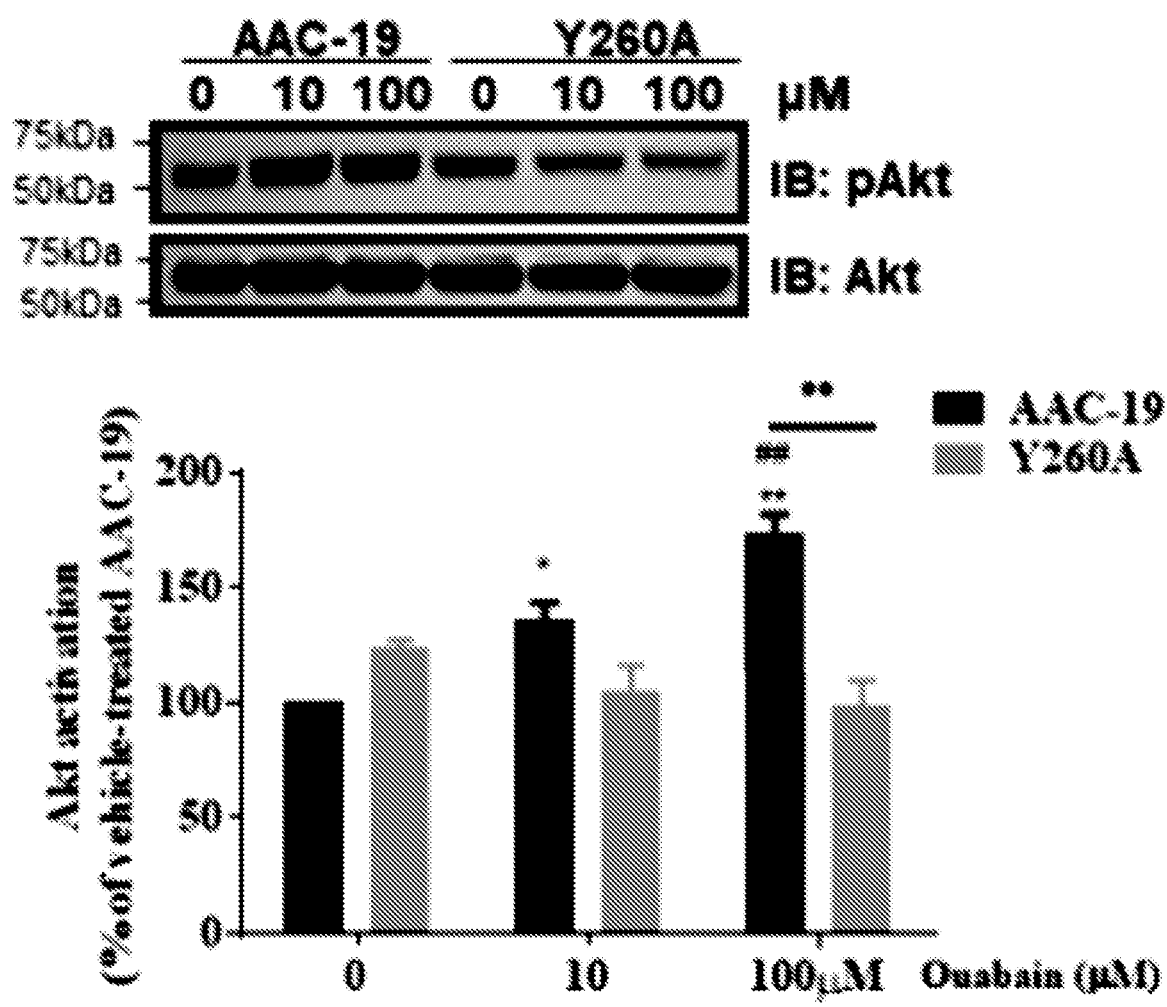
Figure 3D:
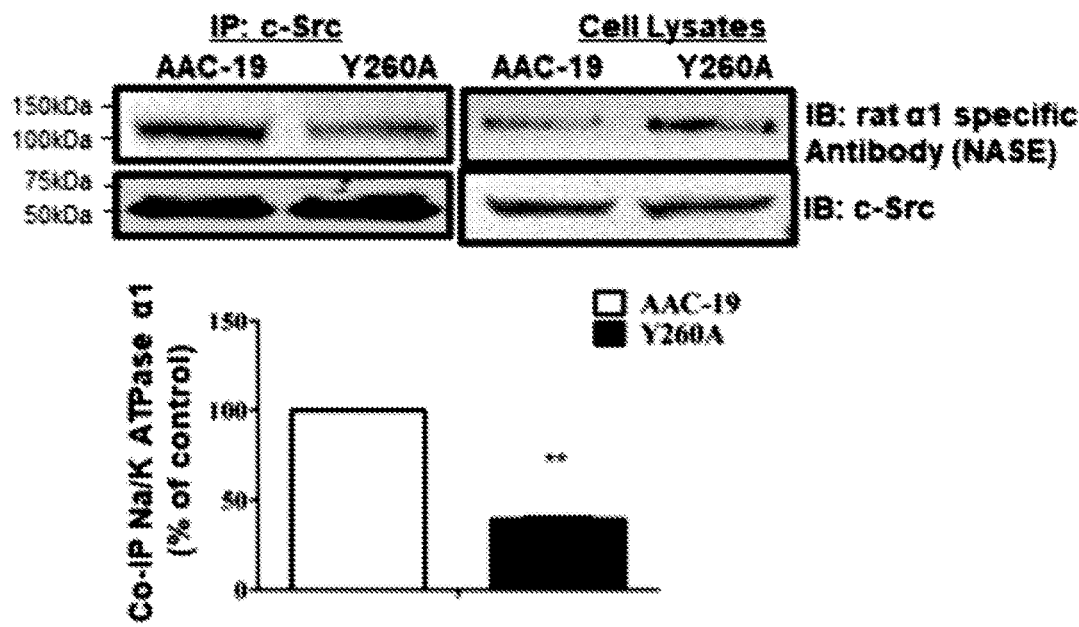
Figure 10A:
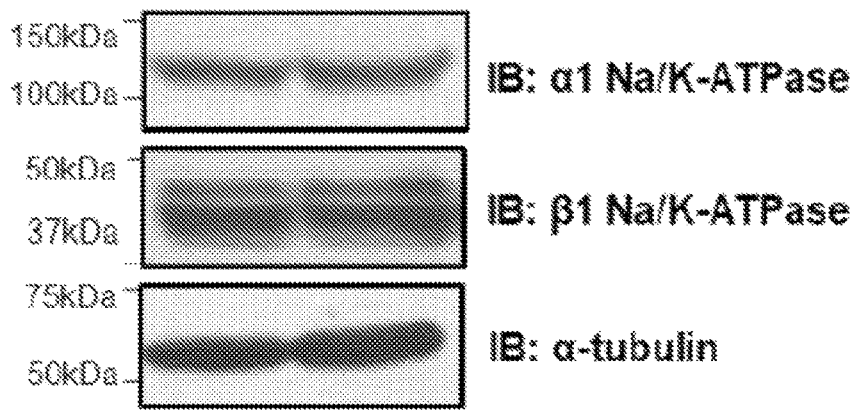
FIGS. 10A-10B include images and a graphs showing.
Figure 10B:
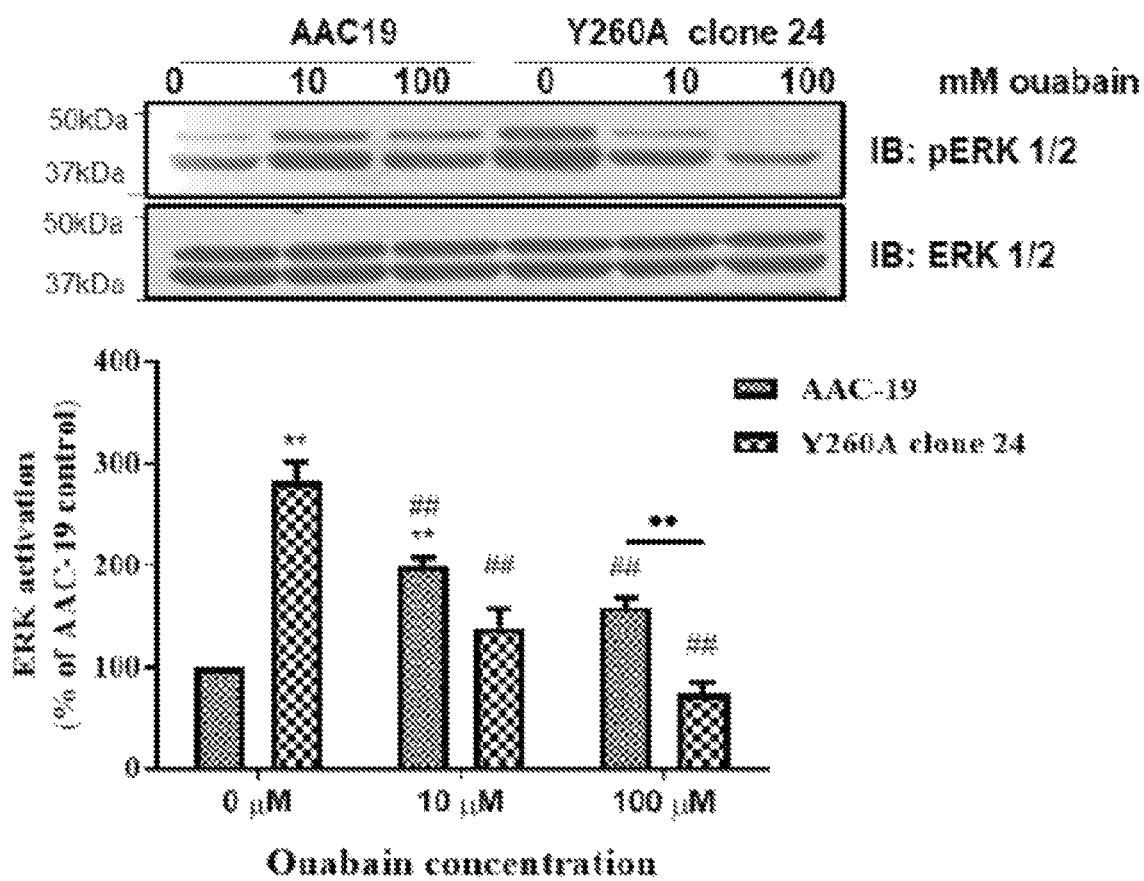

Next, the effects of Y260A mutation were measured in two different signaling pathways where Src plays a role. First, the Y260A mutant and AAC-19 cells were treated with different concentrations of ouabain, and subjected to Western blot measurements of Src, ERK, and Akt activities. Ouabain stimulated Src, ERK and Akt phosphorylation in AAC-19 cells. These stimulations were abolished by the Y260A mutation (FIGS. 3A-3C). To confirm that the observed effect was due to the inhibition of Na/K-ATPase/Src interaction, an immunoprecipitation analysis was conducted. Y260A mutation resulted in a significant decrease (~60%) in the binding of α1 Na/K-ATPase to Src as compared to AAC-19 cells (FIG. 3D). Control experiments showed that another clone of Y260A mutant cells, clone 24, like clone 21, also failed to respond to ouabain stimulation (FIGS. 10A-10B).

Figure 3E:
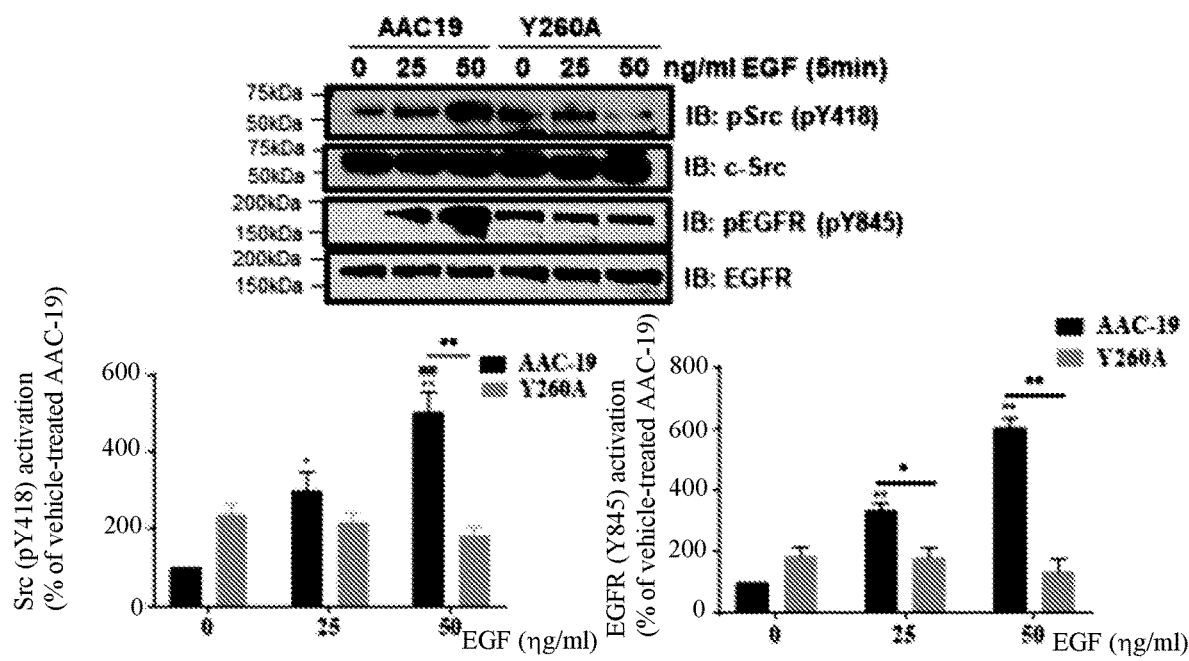

Second, the role of Y260 was assessed in EGFR signaling. Y260A mutant clone 21 and AAC-19 cells were exposed to different concentrations of EGF and measured for EGFR phosphorylation. As depicted in FIG. 3E, EGF stimulated Src kinase activity in AAC-19, but not in Y260A mutant cells. In accordance, EGF stimulated the phosphorylation of EGFR at Y845, a known Src-phosphorylation site 23, in AAC-19, but not in Y260A mutant cells. Interestingly, it was observed that the basal EGFR Y845 phosphorylation was significantly increased in Y260A mutant cells, indicating an important role of Y260-mediated Src interaction in the regulation of basal Src and Src-effector activity.

Figure 9F:
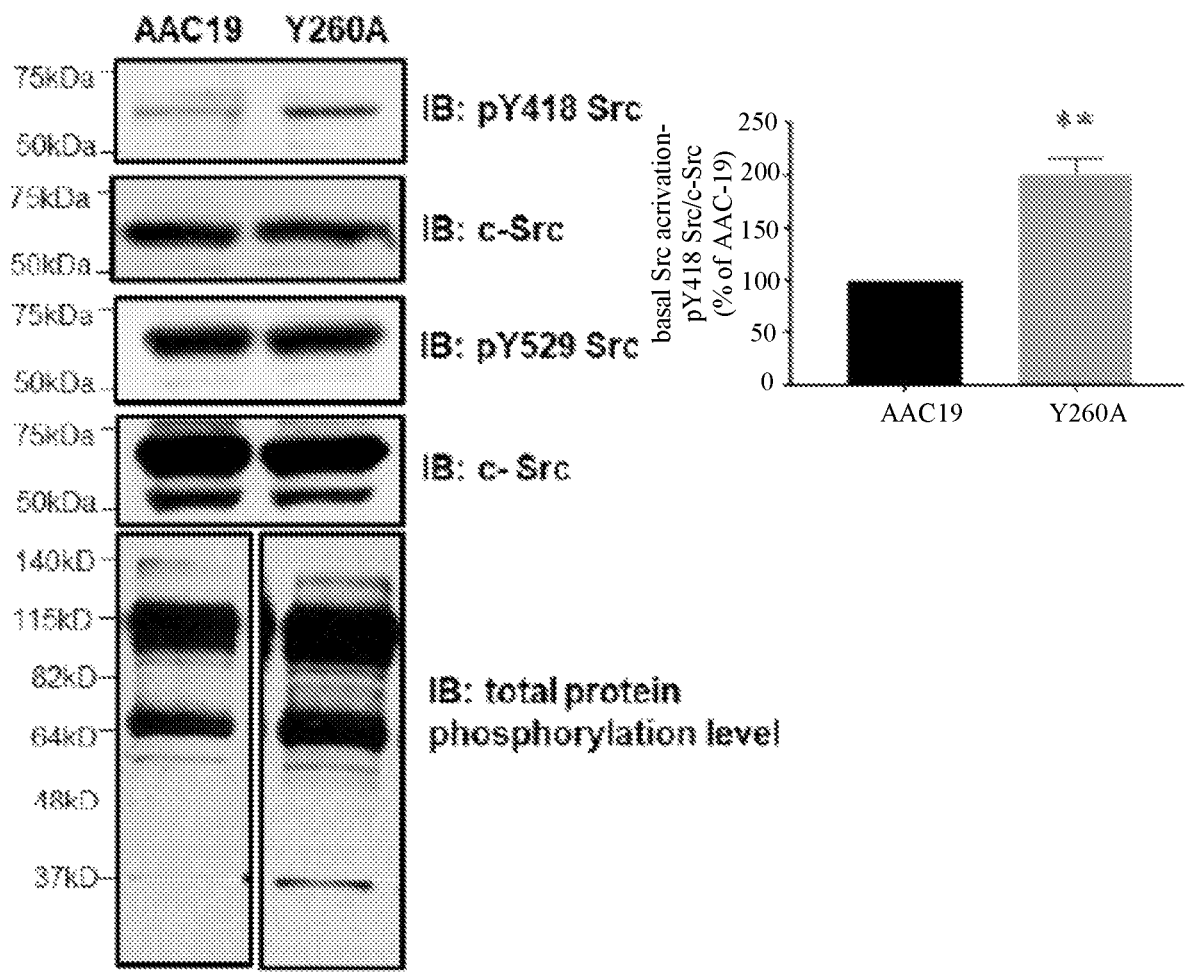
Figure 9G:
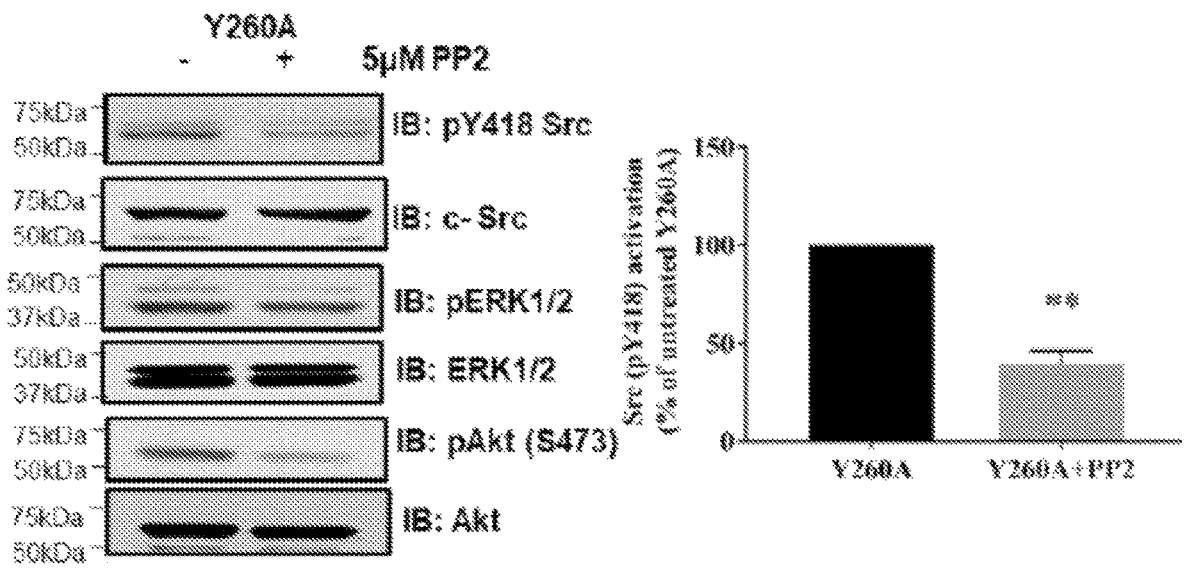

To corroborate this finding, the basal protein tyrosine phosphorylation was first measured. As shown in FIG. 9F, Y260A cells expressed more tyrosine-phosphorylated proteins. To test whether this effect was Src-mediated, Src phosphorylation was measured at Y418 and Y529. As shown in FIG. 9F, Src activity (pY418) was increased almost 2 folds in Y260A cells but there was no change in Y529 phosphorylation. Consistently, basal ERK activities were increased in Y260A cells in comparison to those in AAC-19 cells (FIG. 3B), which was sensitive to PP2, a Src inhibitor (FIG. 9G).

Example 4

Y260A Mutation Leads to Metabolic Switch

The above studies indicated that Y260 phosphorylation was a major regulatory mechanism of Src-mediated signal transduction in the plasma membrane in response to a variety of stimuli. To assess the general significance of this newly discovered signaling mechanism, a potential role of Y260 was probed in the regulation of cellular metabolism.

Figure 4A:
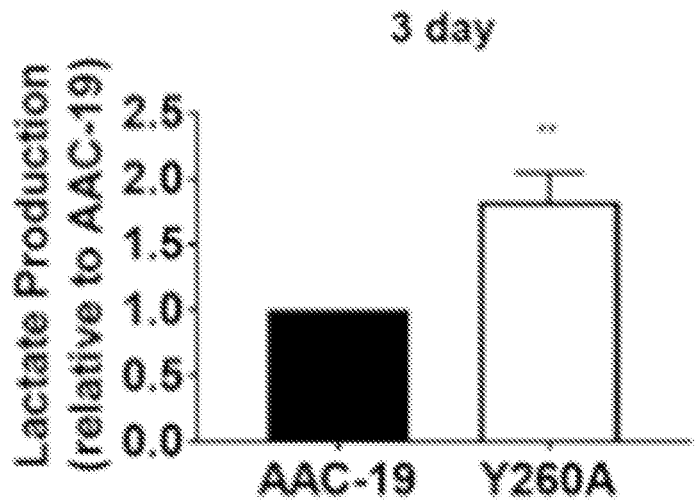
FIGS. 4A-4H include graphs showing the effects of Y260A mutation on cellular metabolism, including.
Figure 4B:
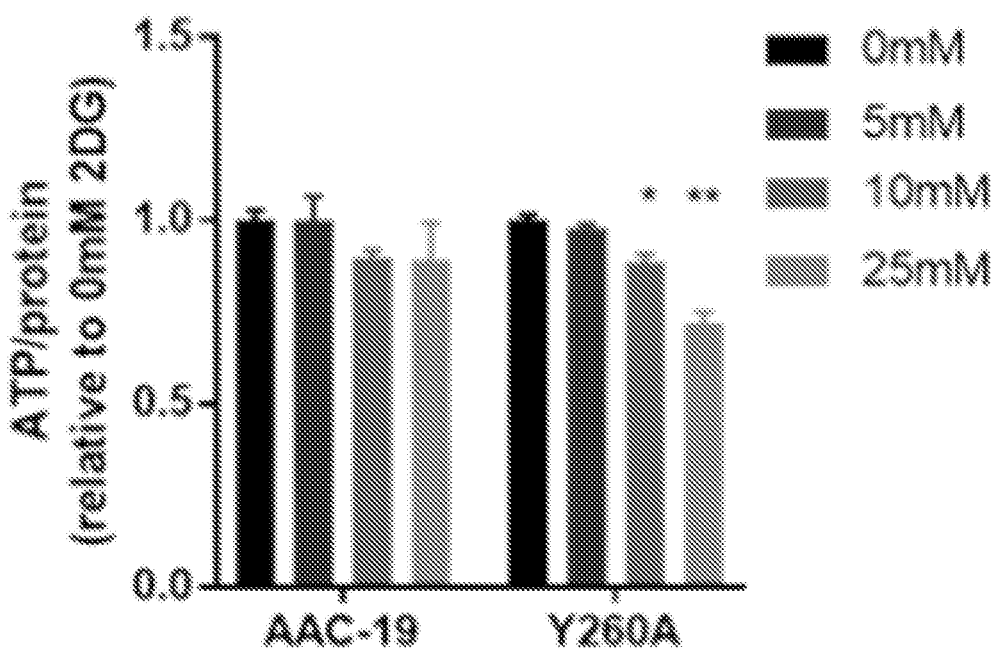
Figure 4C:
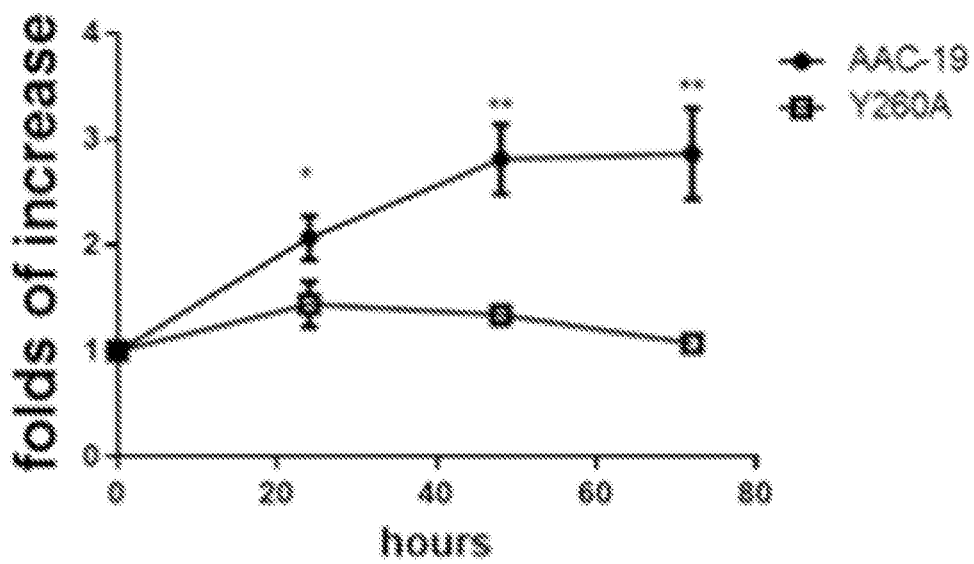

In the routine culture of Y260A mutant cell lines (both clone 21 and 24), faster acidification of culture medium than that of control AAC-19 cells was noticed. Measurement of medium confirmed that Y260A mutant cells produced 80% more lactate than that of AAC-19 cells (FIG. 4A). This suggested that disruption of Y260-mediated Src interaction may cause a metabolic switch from mitochondrial oxidative phosphorylation to aerobic glycolysis. To further test that hypothesis, cellular ATP content in response to the inhibition of glycolysis was first measured by 2-deoxyglucose (2-DG). Compared to AAC-19 cells, Y260A cells were much more sensitive to 2-DG (FIG. 4B). Second, the effect of glucose depletion on cell growth was measured. Y260A mutant cells failed to grow in the absence of glucose whereas AAC-19 cells grew. In fact, the number of AAC-19 cells more than doubled during this time (FIG. 4C).

Figure 4D:
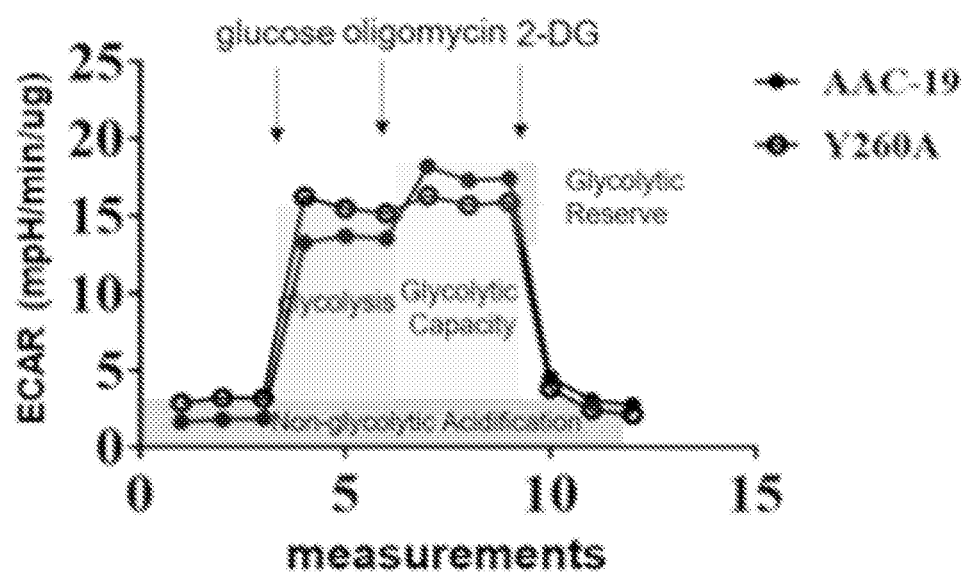
Figure 4E:
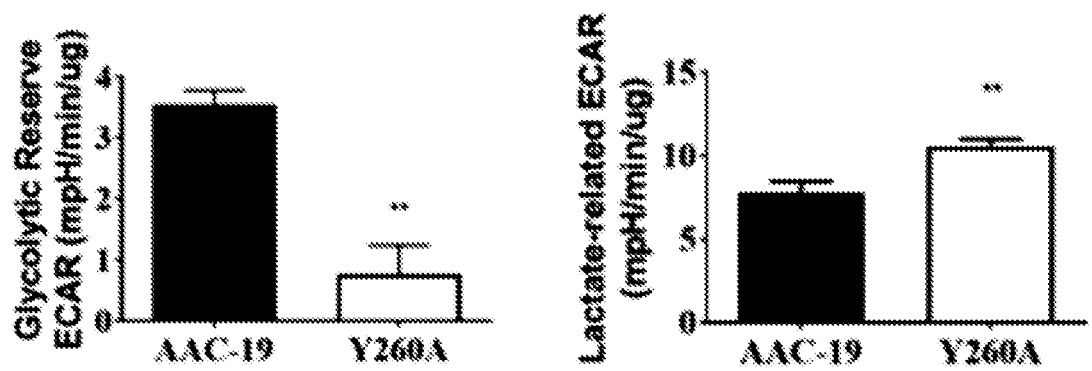
Figure 4F:
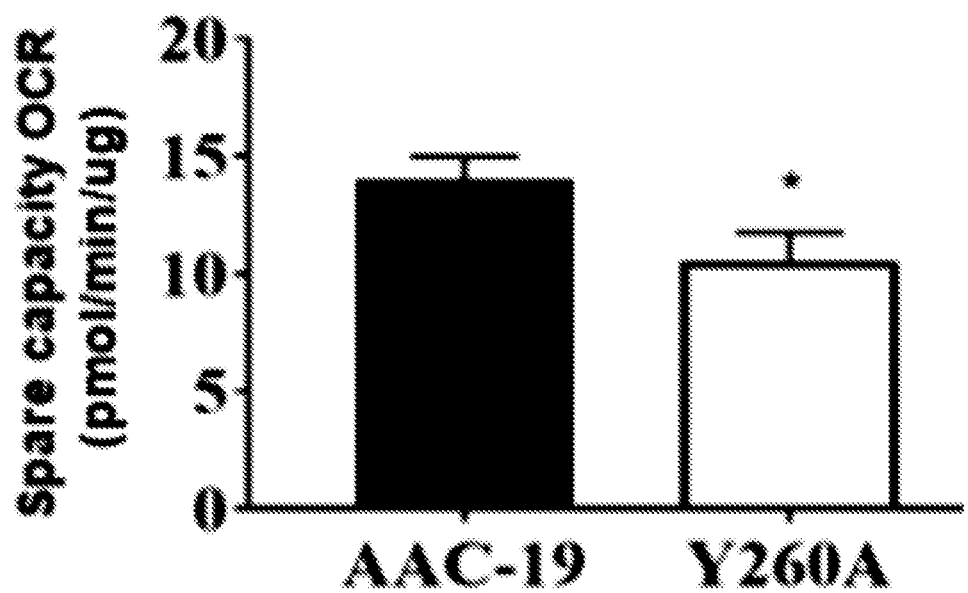
Figure 4G:
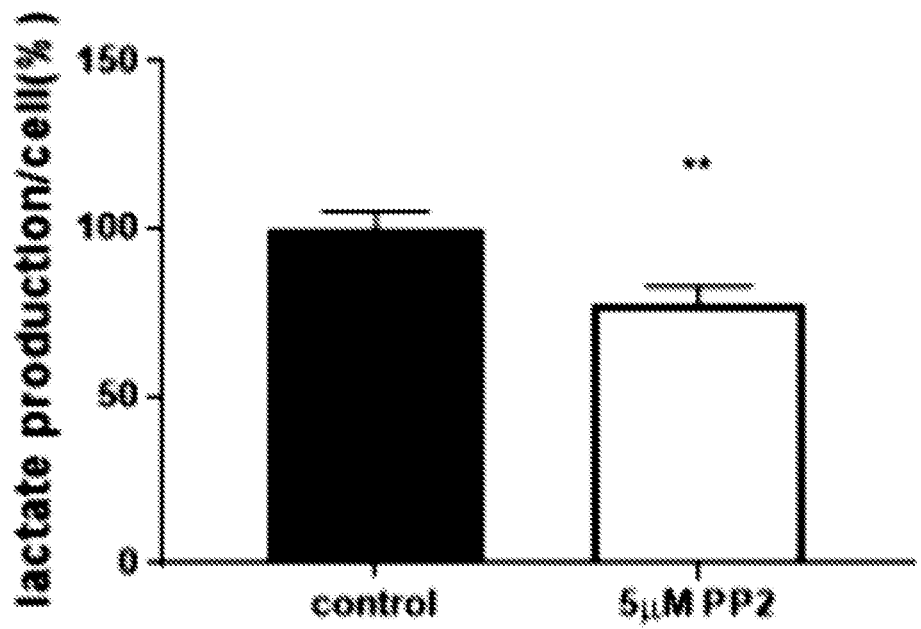
Figure 4H:
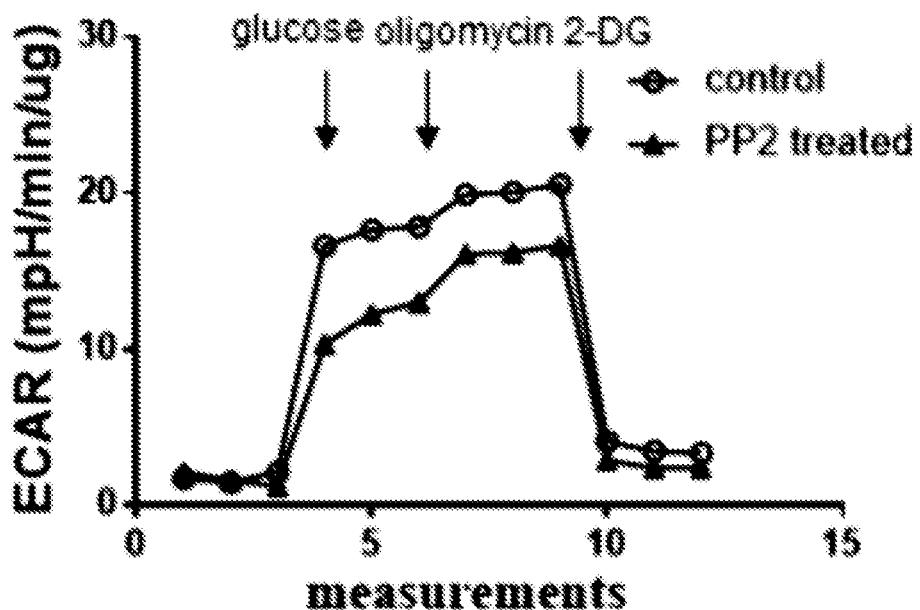

Extracellular acidification rate (ECAR) was then determined in both AAC-19 and Y260A cells in the presence of different inhibitors. Cells were first cultured in glucose-free basal medium. The addition of glucose to cells induced a large increase in ECAR, indicating an increase in aerobic glycolysis (FIG. 4D). To measure the maximal capacity of glycolysis, this was followed by the addition of oligomycin that inhibited mitochondrial ATP production, resulting in a further increase in ECAR in AAC-19, but not in Y260A cells. Moreover, the addition of glycolysis inhibitor 2-DG completely reversed the increase in ECAR. Data analyses indicated a diminished glycolytic reserve in Y260A mutant cells and an increase in aerobic glycolysis (FIG. 4E). When oxygen consumption rate was measured, no major defects in mitochondrial function (e.g. respiratory control ratio and coupling efficiency) were noted (FIGS. 11B-11C) except that the reserve capacity was reduced in Y260A mutant cells (FIG. 4F). Because oncogene activation is known to change cellular metabolic phenotype, it was determined whether this effect was dependent on Src dysregulation by α1 Na/K-ATPase in Y260A cells. As depicted in FIGS. 4G-4H, Src inhibition by treatment of Y260A cells with PP2, a Src inhibitor, was sufficient to reduce both lactate production (FIG. 4G) and glycolysis rate (FIG. 4H).

To further investigate the metabolic adaptation, the gene expression profiles of Y260A mutant cells and control AAC-19 cells were compared by RNAseq analysis. Several important genes involved in the glycolytic metabolism were significantly upregulated in Y260A mutant cells (FIG. 11D). Notably, hexokinase 2 isoform (HK2), pyruvate dehydrogenase kinase (PDK) and lactate dehydrogenase (LDHA) were significantly increased, which has been also observed in cancer cells that underwent metabolic switch. A significant increase in the expression of glucose transporter GLUT4 and a few amino acid transporters in Y260A was also observed, providing further support to the notion that these mutant cells display a metabolic adaptation similar to cancer cells. To further confirm that these effects were mediated by the dysregulation of Src kinase, Y260A cells were treated with PP2 to see if it could reverse the change in metabolic gene expression. As shown in FIG. 11E, PP2 treatment restored the mRNA level of most of these upregulated genes, as measured by qPCR.

Example 5

Y260 Phosphorylation is Reduced in Many Cancer Cell Lines

Figure 5A:
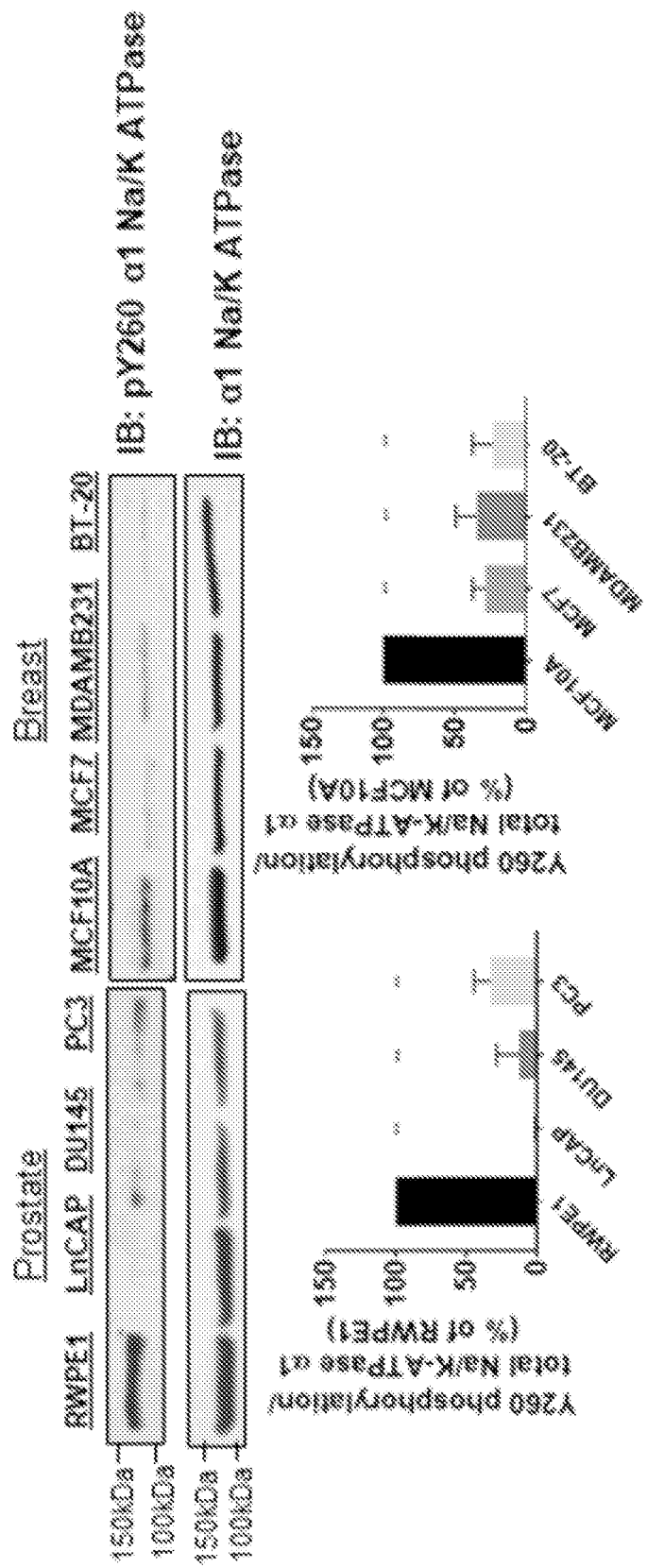
FIGS. 5A-5F include graphs and images showing Y260 phosphorylation and α1 Na/K-ATPase/Src interaction in human cancers, including.

In view of the important role of metabolic switch in cancer biology, the above findings led to the hypothesis that cancer cells may lose the capacity of α1 Na/K-ATPase-mediated Src regulation. To test this hypothesis, the pY260 level was compared in two different panels of cancer cell lines, which should be an indicator of Na/K-ATPase/Src interaction. As shown in FIG. 5A, Y260 phosphorylation was greatly reduced in both prostate and breast cancer cell lines in comparison to the corresponding control cell lines. To verify this, Src kinase was immunoprecipitated in selected cell lines and then co-precipitated α1 Na/K-ATPase level was compared between cancer and control cell lines. A significant decrease in Na/K-ATPase/Src interaction was detected by co-immunoprecipitation (FIG. 12A).

Example 6

Figure 5B:
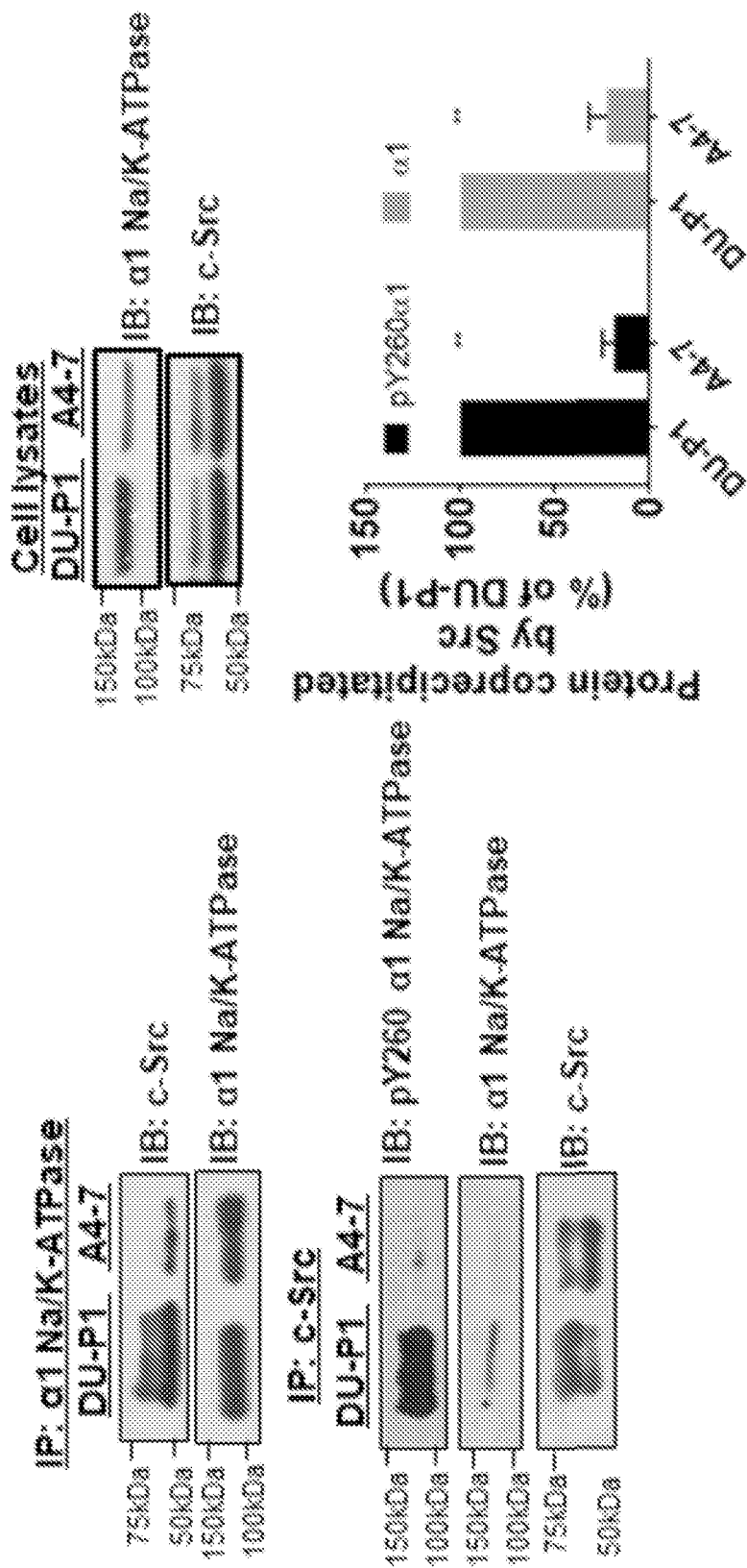
Figure 5C:
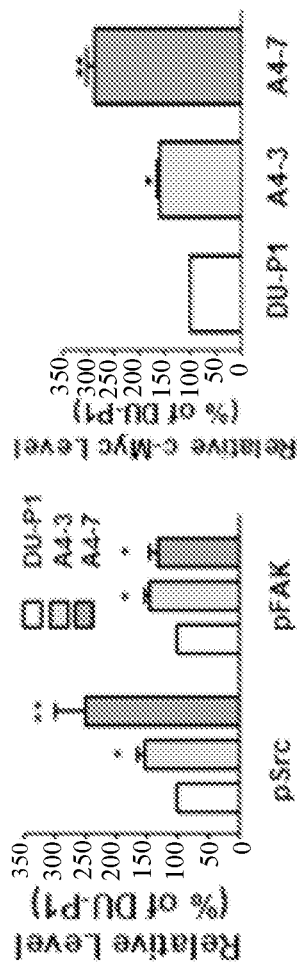
Figure 5C:
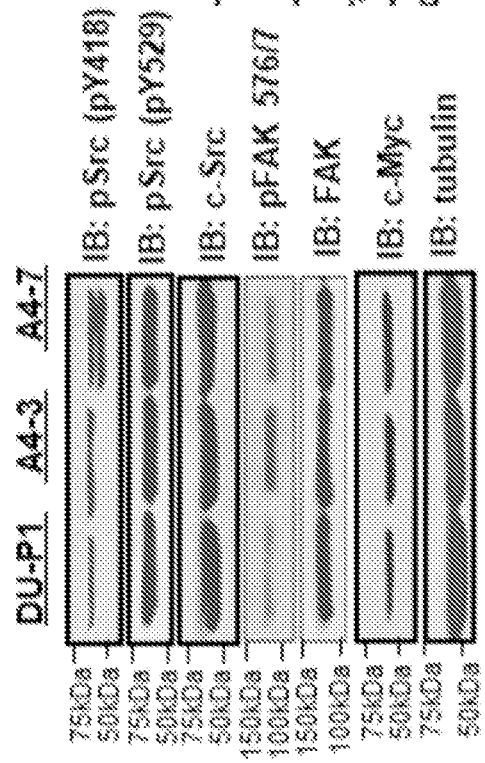
Figure 5D:
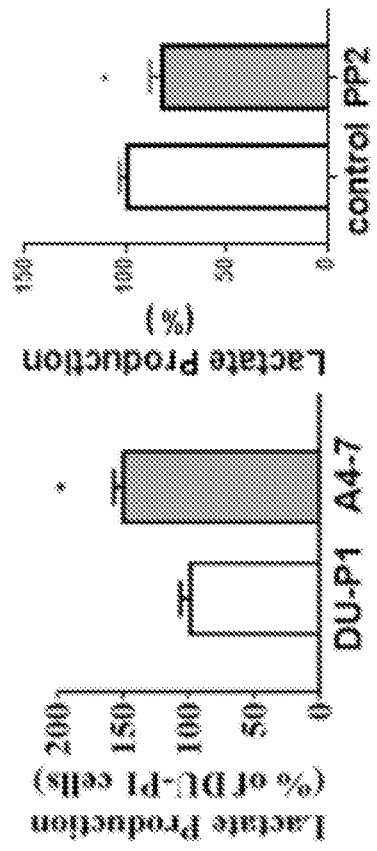
Figure 5E:
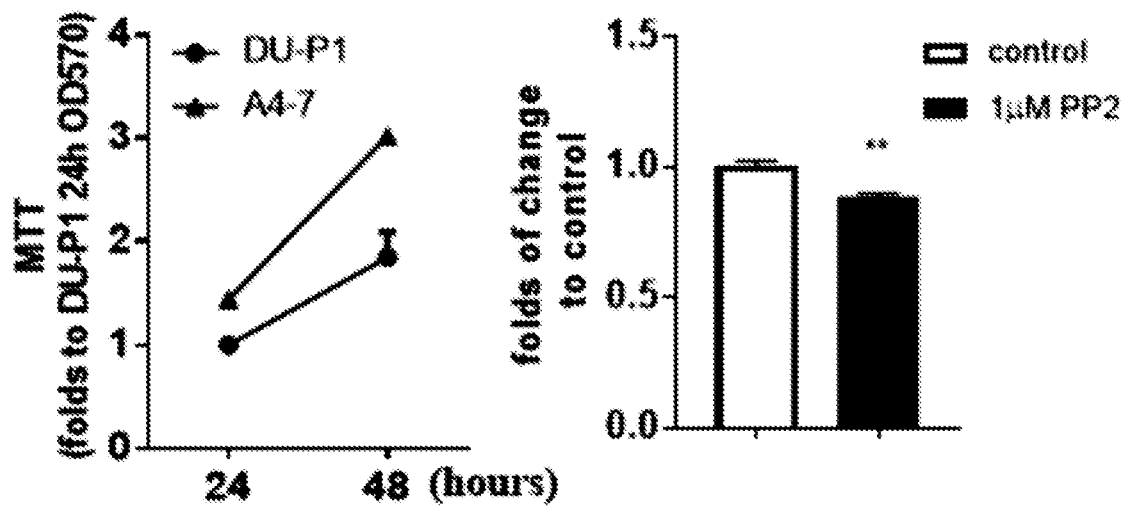
Figure 5F:
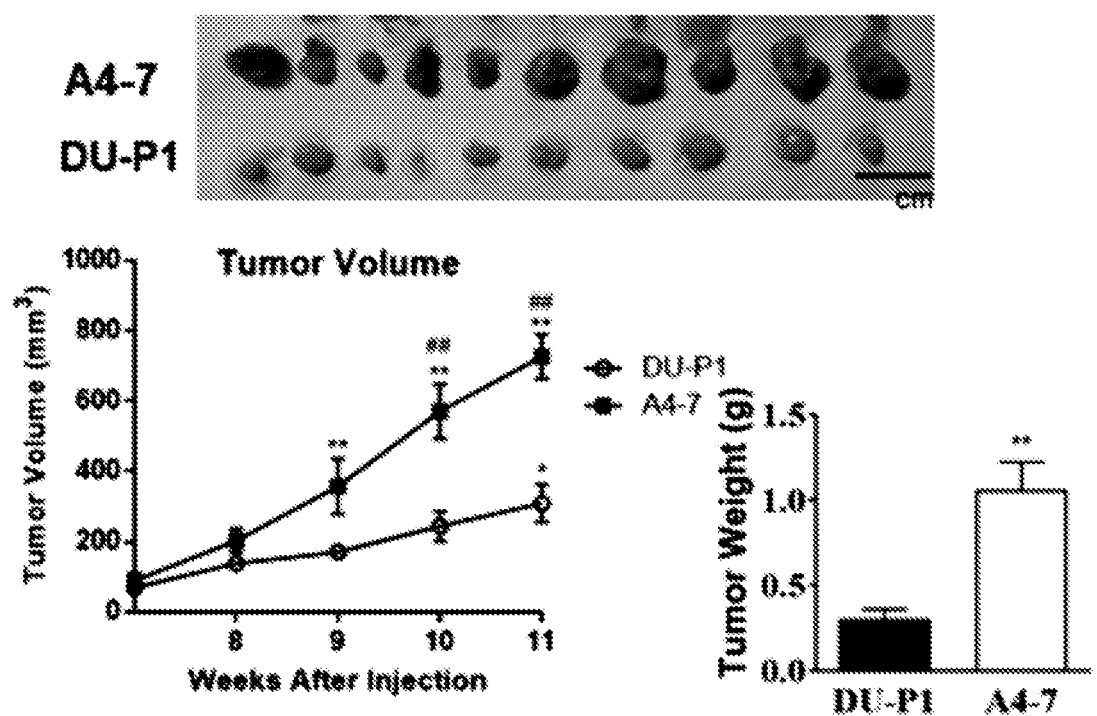
Figure 12B:
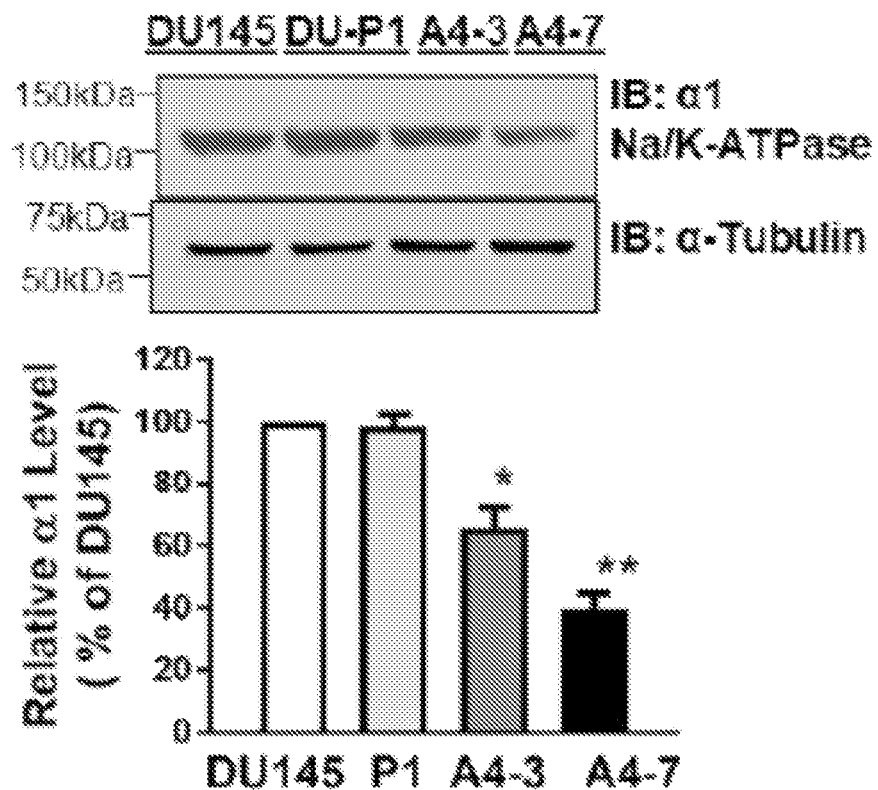
Figure 12C:
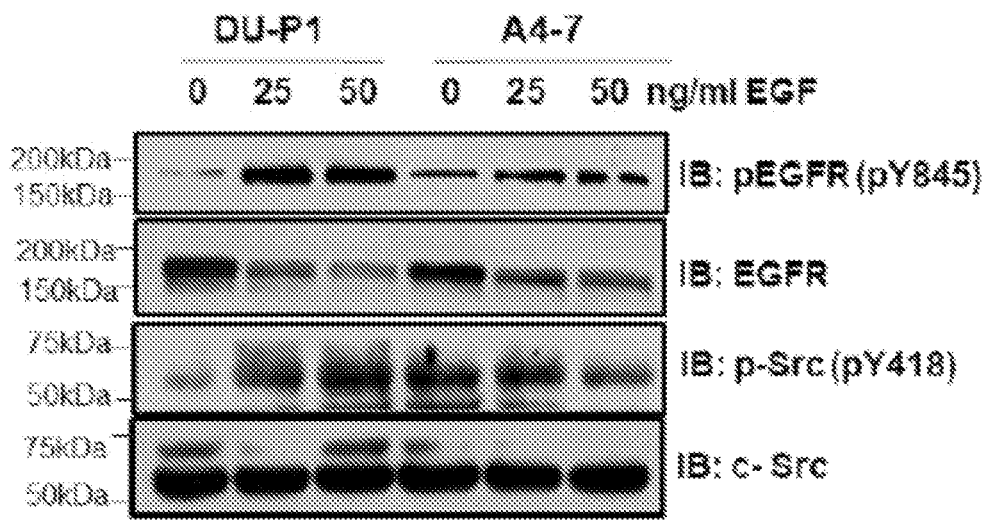
Figure 12D:
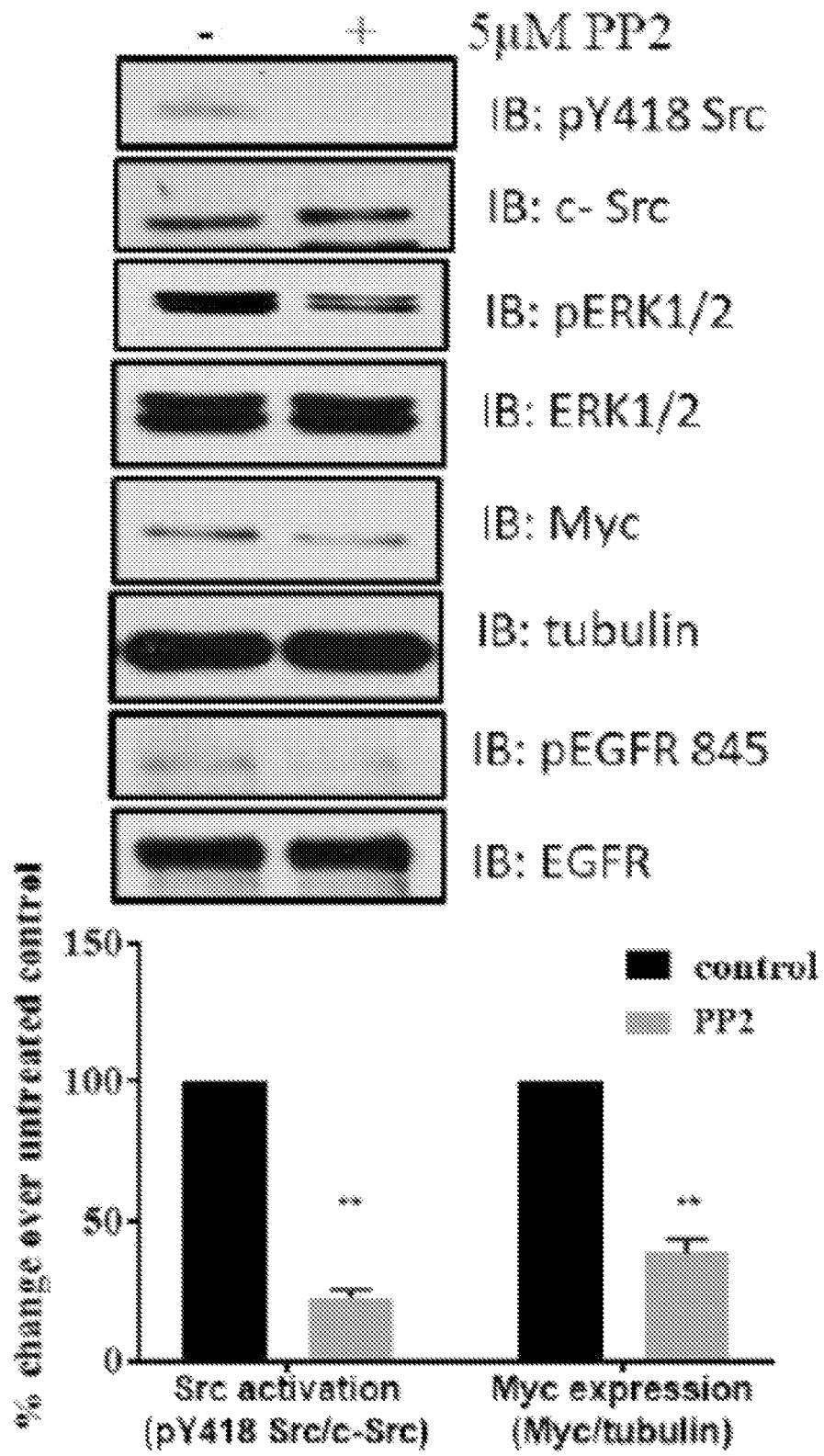
Figure 12E:
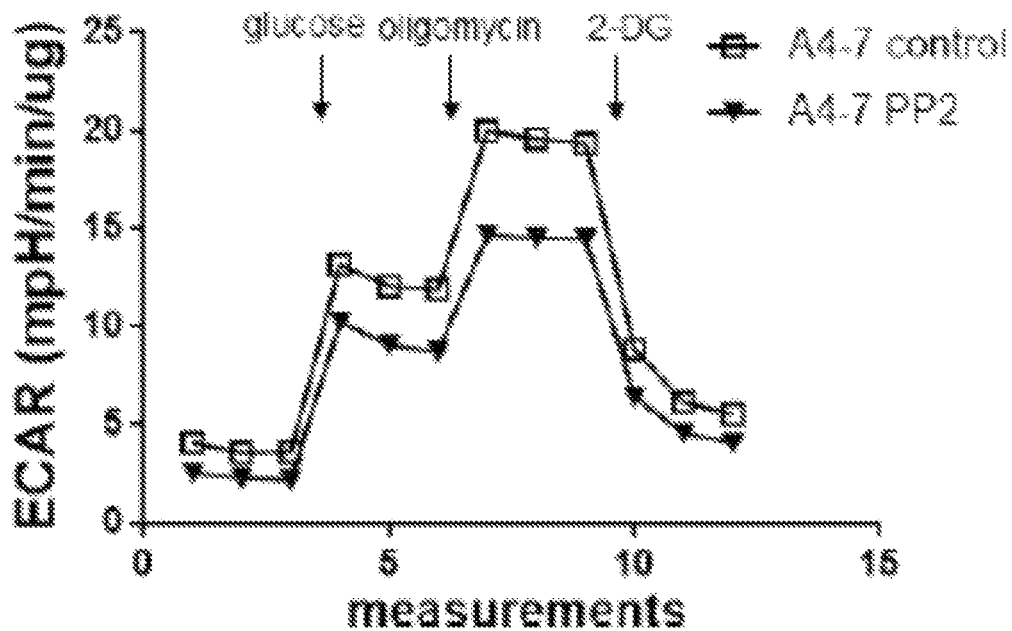

Knocking Down of α1 Na/K-ATPase Increases Aerobic Glycolysis in DU145 Cells and Promotes the Growth of Tumor Xenograft To test whether α1 Na/K-ATPase-mediated Src interaction is important for control of aerobic glycolysis and tumor growth, α1 Na/K-ATPase expression was knocked down in DU145 prostate cancer cells using siRNA and stable cell lines A4-7, A4-3 and a control vector-transfected DU-P1 cell line were generated. The DU-P1 cells expressed similar amount of α1 Na/K-ATPase like parental DU145 cells whereas A4-7 cells showed about 50% down-regulation (FIG. 12B). Functional analyses indicated that knockdown of α1 Na/K-ATPase caused a significant decrease in Na/K-ATPase/Src interaction (FIG. 5B). A significant increase in Src and its effector FAK (Focal Adhesion Kinase) activity was noted in A4-7 cells (FIG. 5C). Moreover, EGF was able to stimulate Src activation and Y845 phosphorylation of EGFR in control DU-P1 cells but not in A4-7 cells (FIG. 12C). Like Y260A mutant cells, basal EGFR Y845 phosphorylation was increased in A4-7 cells. Moreover, A4-7 cells expressed higher amount of Myc, which is indicative of their more aggressive and proliferative nature (FIG. 5C). In accordance, a further increase in lactate production was detected in A4-7 cells, which was sensitive to Src inhibition by PP2 (FIG. 5D and FIG. 12E). To compare the tumor forming ability, the cell proliferation rate of A4-7 cells was tested against DU-P1 cells. The cell proliferation rate of A4-7 was significantly higher than that of the control, and reversed by PP2 (FIG. 5E). Finally, when control DU-P1 and A4-7 cells were implanted into NOD/SCID mice, a close to four-fold increase in tumor size of A4-7 vs DU-P1 was observed (FIG. 5F).

Example 7

Figure 6A:
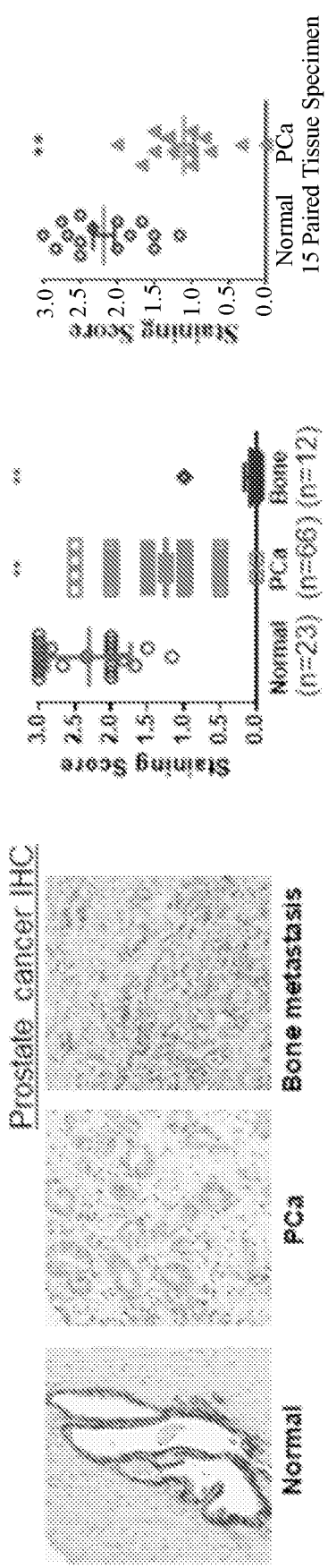
FIGS. 6A-6E include images and graphs showing the measurement of α1 Na/K-ATPase expression in primary tumor and metastatic lesions, including.
Figure 6B:
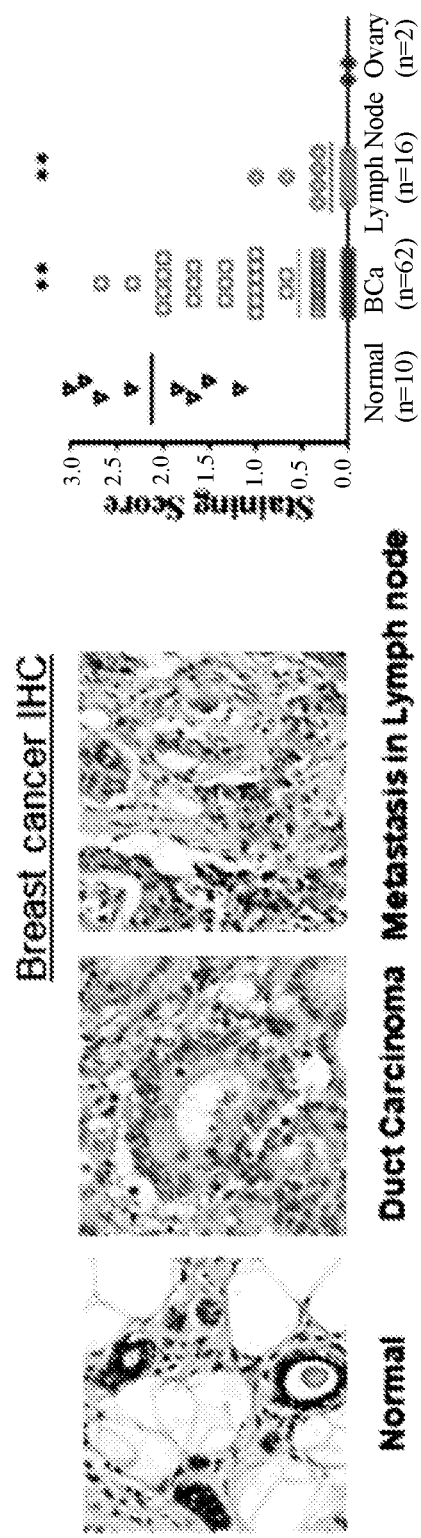
Figures 6C, 6D:
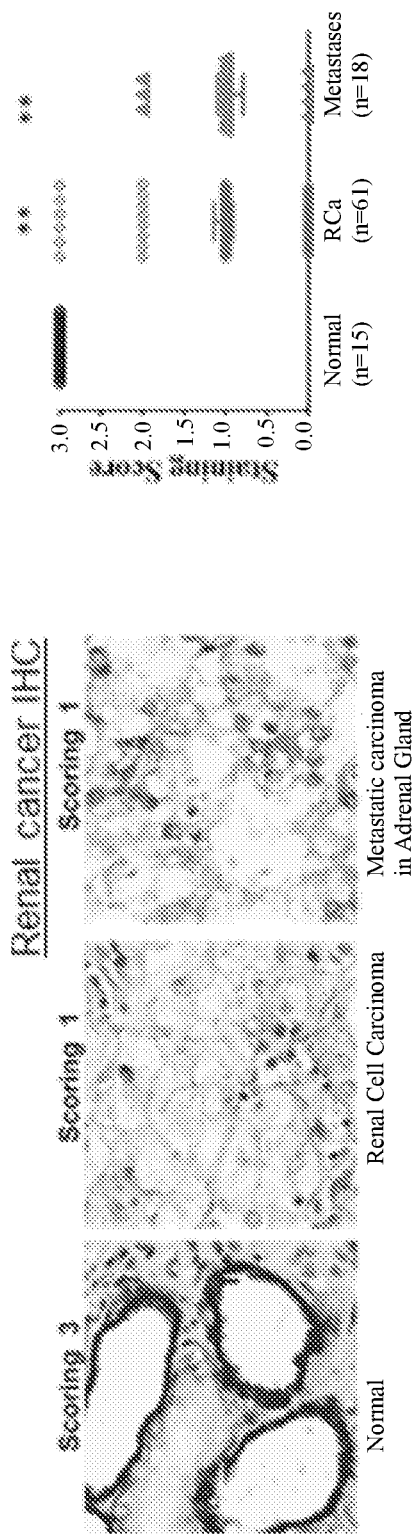

Expression of α1 Na/K-ATPase is Reduced in Several Human Cancers, Especially the Metastatic Lesions To assess the clinical relevance of the above-described findings, α1 protein expression was measured in three different types of human cancer where the expression of al Na/K-ATPase in the normal epithelium is high. First, 66 prostate carcinoma, 12 bone metastatic and 23 normal tissue samples were analyzed. The expression of α1 Na/K-ATPase was significantly reduced (FIG. 6A) in prostate carcinoma (n=66) vs control (n=23). This was confirmed by paired analyses (normal vs carcinoma, n=15). More importantly, there were no detectable α1 Na/K-ATPase signals in 11 out of 12 bone metastatic samples. Second, 10 normal breast tissue and 62 ductal carcinoma samples were compared along with corresponding metastatic samples in the ovary and lymph node (FIG. 6B). The expression of α1 Na/K-ATPase was significantly decreased in the primary tumor and further reduced in metastatic samples. Third, a significant decrease in α1 Na/K-ATPase expression was also found in renal cell carcinoma (n=61) in comparison with the control (n=15) (FIG. 6C). Interestingly, a decrease in adrenal gland metastasis of renal carcinoma appeared to be less severe than that in bone lesions of prostate cancer. However, α1 Na/K-ATPase was highly expressed in normal kidney tubules (15 out of 15 scored 3 in normal tissue). This level of expression was detected in only about 10% of renal cell carcinoma (6 out of 61) and further reduced to 0% in metastatic lesions.

Figure 6E:
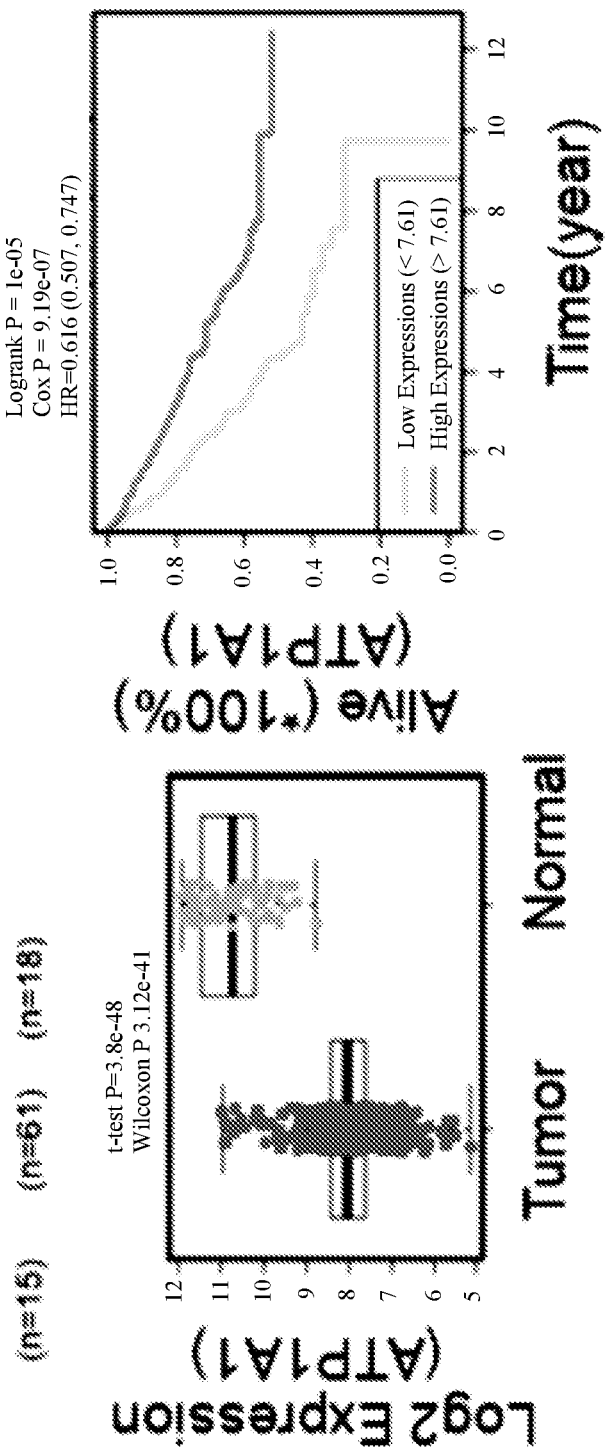
Figure 13A:
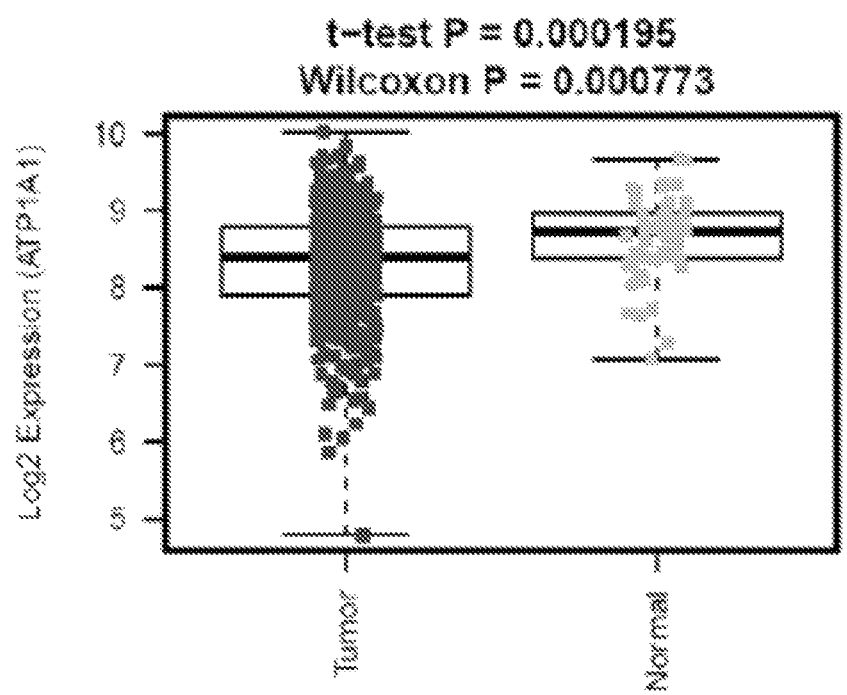
FIGS. 13A-13B include graphs showing.
Figure 13B:
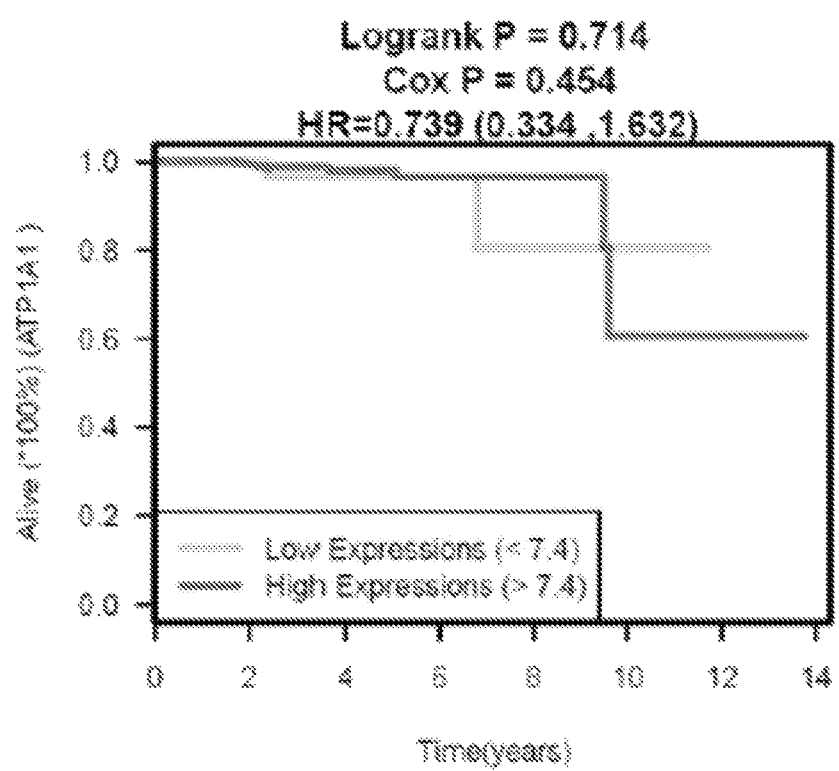
Figure 14:
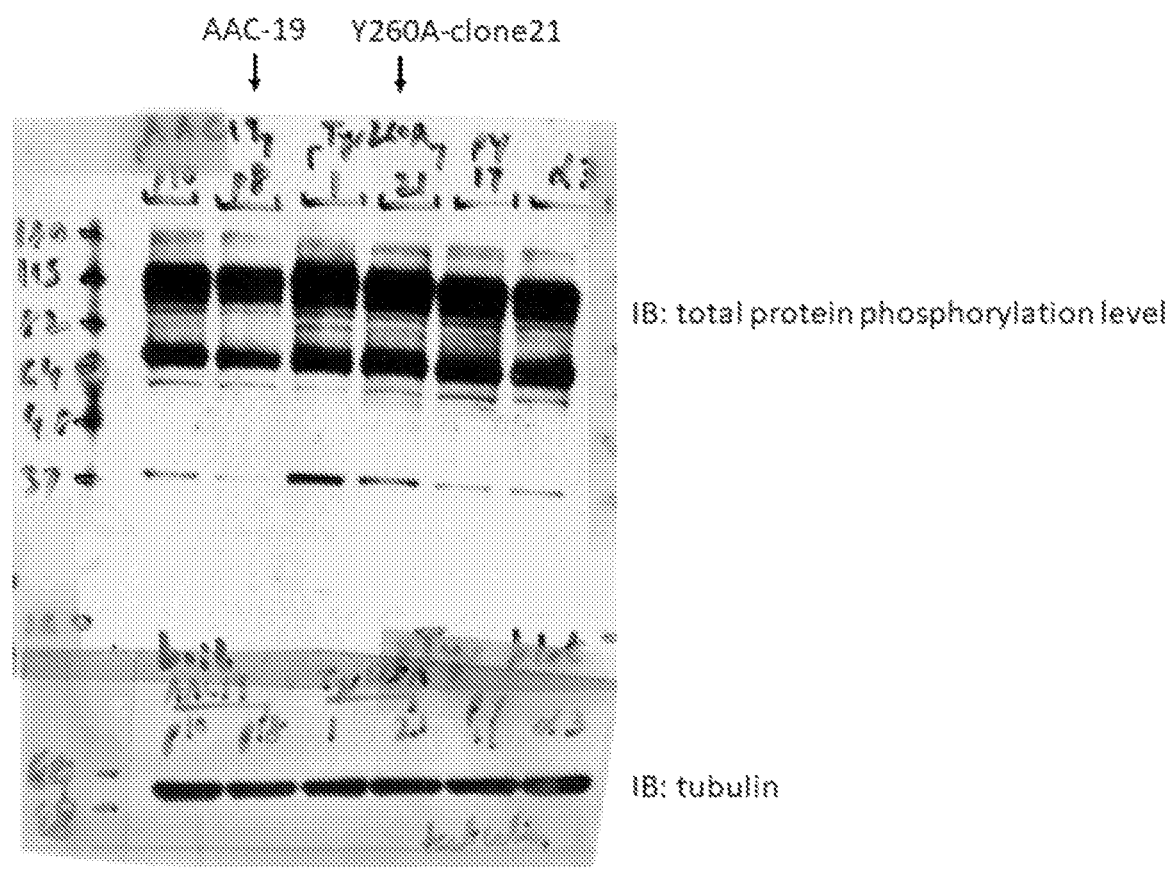
FIG. 14 is a graph showing a full-length blot of the total protein phosphorylation level in FIG. 9F.

Transcriptional regulation could represent an important mechanism of changing al expression in human cancers. Database searches revealed that the expression of α1 Na/K-ATPase mRNA was significantly reduced (p<0.001) in renal clear cell carcinoma in the TCGA-KIRC database (n=530). The mean log 2 values are 11 and 8.4 for the normal kidney and renal carcinoma, respectively. Most importantly, this expression pattern inversely correlated with patient survival rate, with lower expression being associated with a high mortality rate (FIG. 6E). A significant decrease in the expression of α1 Na/K-ATPase mRNA in prostate cancer was also detected. However, the difference was less than 0.3 Log 2 value. As such, there was no correlation between lowered mRNA expression and patient survival rate in prostate cancer (FIGS. 13A-13B).

Discussion of Examples

Figure 7:
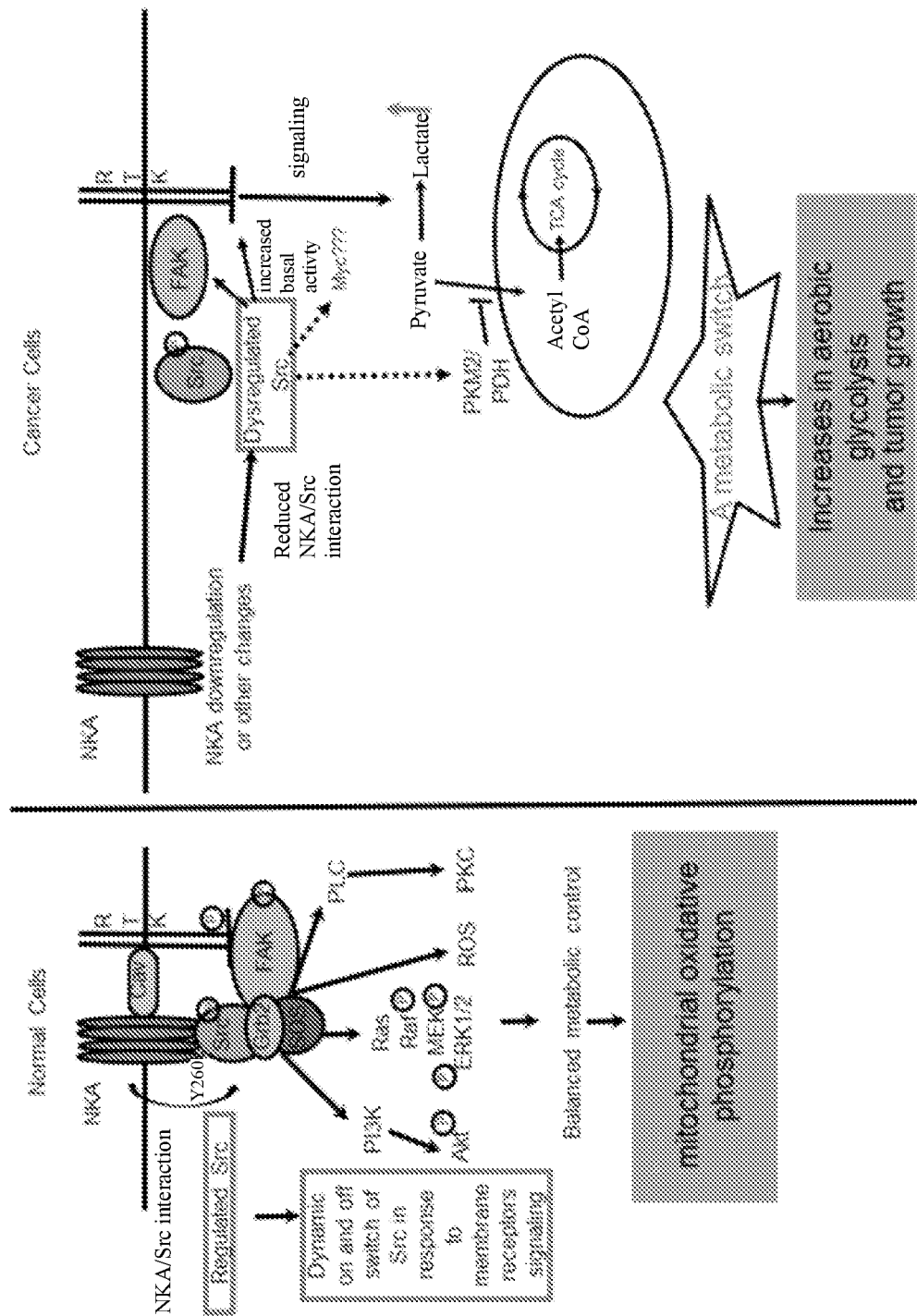
FIG. 7 is a schematic diagram showing α1 Na/K-ATPase-mediated Src regulation in normal and cancer cells, where established signaling pathways are denoted by solid black arrows and speculated signaling pathways are denoted by broken black arrows (NKA=Na/K-ATPase, Cav=Caveolin 1, FAK=Focal Adhesion Kinase, RTK=Receptor Tyrosine Kinase, PI3K=Phosphatidyl Inositol 3 Kinase, ROS=Reactive Oxygen Species, PLC=Phospholipase C, PKC=Protein Kinase C, PKM2=Pyruvate Kinase isoenzyme M2, PDH=Pyruvate Dehydrogenase, ERK=Extracellular Regulatory Kinase), and where the circled letter P denotes phosphorylation and activation.

The above examples describe the discovery of α1 Na/K-ATPase Y260 as a Src-specific phosphorylation and binding site, and an increase in Y260 phosphorylation as a general feature of Src-mediated signal transduction in response to the activation of membrane receptors. It appears that this dynamic regulation of Src by α1 Na/K-ATPase is significantly attenuated or lost in human cancer cells. This dysregulation increases the basal Src activity, resulting in the activation of Src effectors such as ERK, EGFR, Akt and FAK, all of which are implicated in cancer progression. Furthermore, the foregoing Examples provide evidence that the loss of Src regulation by α1 Na/K-ATPase causes a metabolic switch and promotes the formation and growth of tumor xenograft. A schematic diagram of α1 Na/K-ATPase-mediated Src regulation and the consequence of the loss of this regulation is given in FIG. 7. These and other important issues are further discussed.

Na/K-ATPase α1 isoform as an underappreciated albeit important regulator of Src family kinases: Recent studies have indicated an important role of α1 Na/K-ATPase-mediated and Src-dependent pathways in control of embryonic development, renal salt handling and in disease progression where inflammation and ROS stress play an important role. Interestingly, it appears that α1 Na/K-ATPase also interacts with other members of Src family kinases and that such interaction (e.g., Lyn) is a key to CD36- and CD40-mediated signal transduction. The new findings presented herein above affirm the ability of α1 Na/K-ATPase to bind and regulate Src. Specifically Y260 and its phosphorylation by Src kinase appears to be significant in many Src kinase mediated signaling pathways, since it participated in not just ouabain, but also EGF as well as integrin signaling. These data indicated that α1 Na/K-ATPase is a partner (regulator) of Src kinase in the plasma membrane, which is further supported by the loss of function Y260A mutant studies. Moreover, the Y260A mutant Na/K-ATPase is fully functional as an ion pump, but defective in binding and regulating Src. As such, it blocks not only ouabain but also EGF-induced Src signaling. Moreover, it also caused Src dysregulation as basal Src activity increased by almost 2 folds in Y260A cells. Concomitantly, an increase in activity of ERK was detected, which was sensitive to Src inhibitor, PP2 (FIG. 9G). These findings were consistent with prior observations that either knockdown of α1 Na/K-ATPase or expression of Src binding-al mutants increases basal Src and consequently ERK activity. Thus, the new findings affirm the contention that the α1 Na/K-ATPase is a major regulator of the plasma membrane pool of Src. Without wishing to be bound by any particular theory or mechanism, it is further believed that the loss of interaction between α1 Na/K-ATPase and Src will result in a dysregulation of Src, which could lead to the inability of ouabain-induced signaling and to increased basal Src activity.

Although many proteins interact and regulate Src, α1 Na/K-ATPase appears to be the only one that can regulate Src simultaneously through its two domain-domain interactions. This balanced and sequential regulation is essential for the dynamic nature of Src signaling. Disruption of either interaction alters Src signaling regardless of whether basal Src activity is increased or decreased, resulting in changes in cellular metabolism and growth.

The role of α1 Na/K-ATPase in the regulation of aerobic glycolysis and its implication in cancer biology: Although mutations in oncogenes like KRAS or PI3K genes have been implicated in the metabolic switch observed in cancer cells, how dysregulations of the proto-oncogene SRC affects tumor growth is not clear. Src family kinases (SFK) are frequently hyper-activated in cancers but activating mutations or chromosomal rearrangements in Src are relatively rare in nature. The precise molecular mechanism underlying the defective Src regulation in human cancers remains to be resolved.

Interestingly, Y260A mutant cells undergo a metabolic switch from mitochondrial oxidative phosphorylation to aerobic glycolysis (i.e., an increase in lactate production), a phenomenon commonly seen in oncogenic cells. The expression of several important glycolytic genes is upregulated in these cells, which further supports the phenotype. Consistently, PP2 treatment not only reduced the expression of these up-regulated genes involved in glycolysis, but also blocked the increase in lactate production (FIGS. 4G-4H). In short, these studies provide a molecular insight of how α1 Na/K-ATPase may work as a regulator of cellular metabolism through Src.

It is further believed that this mechanism may provide a novel link connecting Na/K-ATPase α1 subunit downregulation in cancer to defective Src regulation and henceforth altered cellular metabolism. The above studies demonstrate that cells harboring Y260A mutant Na/K-ATPase have increased aerobic glycolysis and lactate production. Y260 phosphorylation was significantly reduced in human cancer cell lines, indicating a loss of Src regulation by α1 Na/K-ATPase. This finding is further substantiated by the tissue array data that show a significant decrease in α1 Na/K-ATPase in three different types of human cancers. Others have also reported a reduction in Na/K-ATPase α1 expression in lung, skin and testicular cancers. Apparently, both transcriptional (e.g., kidney) and post-transcriptional mechanisms (e.g., prostate) are involved in the down-regulation of α1 Na/K-ATPase. The post-transcriptional regulation appears to involve increased endocytosis of α1 Na/K-ATPase.

The importance of α1 Na/K-ATPase in cancer biology was further substantiated by two additional observations. First, the expression of α1 Na/K-ATPase is further reduced in metastatic samples from prostate, breast cancer, and renal cell carcinoma. Src activity is higher in metastatic lesions relative to primary tumor tissues. It is plausible that the decrease in the expression of α1 Na/K-ATPase diminishes the regulation of Src, leading to an increase in basal Src activity. This is supported by the data that Src and its effectors such as EGFR and FAK activity were further increased in α1 knockdown A4-7 cells (FIG. 5C and FIG. 12C). Moreover, A4-7 cells had increased lactate production and c-Myc expression (FIGS. 5C-5D), which is indicative of their more aggressive status. This is reaffirmed by an almost four-fold increase in tumor size when xenografted into mice (FIG. 5F). This observation is consistent with knockdown studies reported with other Src regulators like Csk. Second, data analysis of renal clear cell carcinoma in the TCGA-KIRC database (n=530) reveals a significant decrease in the expression of α1 mRNA in patient samples. This decrease is inversely correlated with the survival of patients suffering from renal clear cell carcinoma.

Figure 11A:
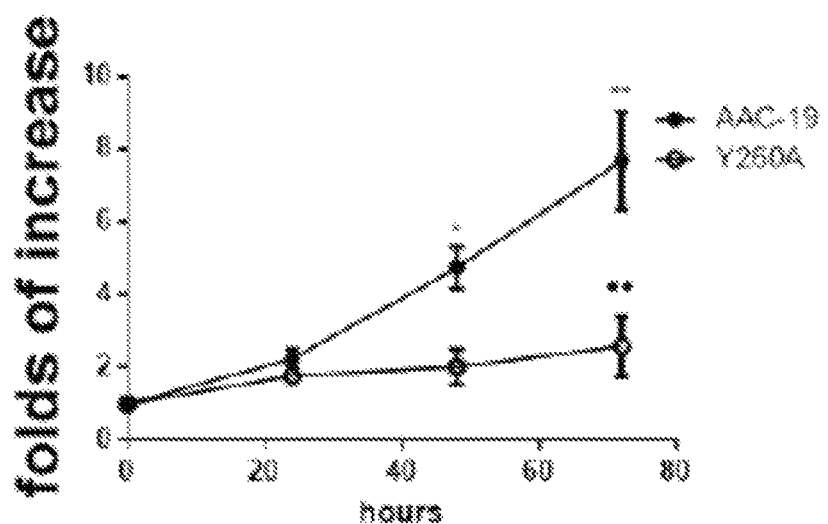
Figure 11B:
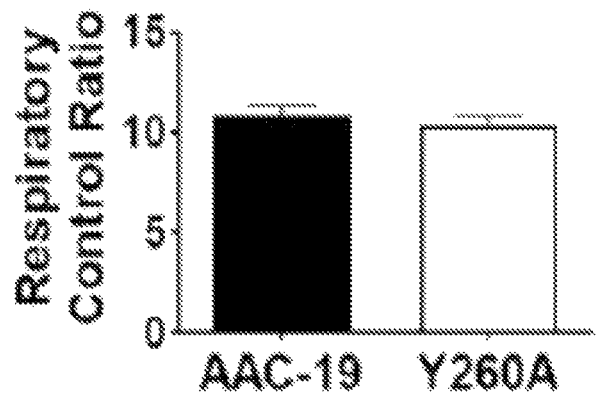
Figure 11C:
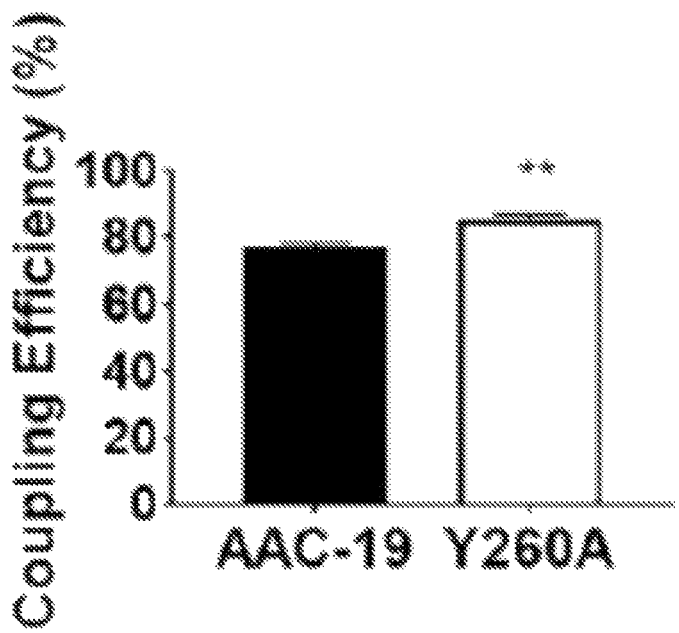

In short, the new findings provide strong evidence that α1 Na/K-ATPase works like a tumor suppressor by regulating the cellular Src kinase. Furthermore, it is thought that Y260 phosphorylation may be utilized as an indicator for Na/K-ATPase/Src interaction in cancers. This may be of importance in some cancer types where α1 Na/K-ATPase expression is reportedly high. Finally, it is important to note that although the metabolic switch is well established to play a role in tumorigenesis, the data do not allow us to conclude that increases in tumorigenesis in A4-7 cells are due to increased glycolysis. Interestingly, it was observed that this switch actually inhibits cell proliferation in Y260A cells (FIG. 11A). This apparent discrepancy in cellular fate may be explained by the recent findings that suggests activation of oncogene in normal cells can induce them to enter a non-proliferative state called senescence, whereas oncogene activation in cancer cells can cause them to become hyper proliferative.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. DeNicola, G. M. & Cantley, L. C. Cancer's Fuel Choice: New Flavors for a Picky Eater. Molecular cell 60, 514-523, doi:10.1016/j.molcel.2015.10.018 (2015).
2. Irby, R. B. & Yeatman, T. J. Role of Src expression and activation in human cancer. Oncogene 19, 5636-5642, doi:10.1038/sj.onc.1203912 (2000).
3. Liang, J. et al. PKM2 dephosphorylation by Cdc25A promotes the Warburg effect and tumorigenesis. Nat Commun 7, 12431, doi:10.1038/ncomms12431 (2016).
4. Zhang, J. et al. c-Src phosphorylation and activation of hexokinase promotes tumorigenesis and metastasis. Nat Commun 8, 13732, doi:10.1038/ncomms13732 (2017).
5. Jin, L. et al. Phosphorylation-mediated activation of LDHA promotes cancer cell invasion and tumour metastasis. Oncogene 36, 3797-3806, doi:10.1038/onc.2017.6 (2017).
6. Cairns, R. A., Harris, I. S. & Mak, T. W. Regulation of cancer cell metabolism. Nature reviews. Cancer 11, 85-95, doi:10.1038/nrc2981 (2011).
7. Liang, M. et al. Identification of a pool of non-pumping Na/K-ATPase. The Journal of biological chemistry 282, 10585-10593 (2007).
8. Lingrel, J. B. The physiological significance of the cardiotonic steroid/ouabain-binding site of the Na,K-ATPase. Annu Rev Physiol 72, 395-412, doi:10.1146/annurev-physiol -021909-135725 (2010).
9. Blanco, G. & Wallace, D. P. Novel role of ouabain as a cystogenic factor in autosomal dominant polycystic kidney disease. American journal of physiology. Renal physiology 305, F797-812, doi:10.1152/ajprenal.00248.2013 (2013).
10. Cui, X. & Xie, Z. Protein Interaction and Na/K-ATPase-Mediated Signal Transduction. Molecules (Basel, Switzerland) 22, doi:10.3390/molecules22060990 (2017).
11. Tian, J. et al. Binding of Src to Na+/K+-ATPase forms a functional signaling complex. Molecular biology of the cell 17, 317-326 (2006).
12. Ye, Q. et al. Identification of a potential receptor that couples ion transport to protein kinase activity. The Journal of biological chemistry 286, 6225-6232, doi:10.1074/jbc.M110.202051 (2011).
13. Ye, Q. et al. Expression of mutant alpha1 Na/K-ATPase defective in conformational transition attenuates Src-mediated signal transduction. The Journal of biological chemistry 288, 5803-5814, doi:10.1074/jbc.M112.442608 (2013).
14. Li, Z. & Xie, Z. The Na/K-ATPase/Src complex and cardiotonic steroid-activated protein kinase cascades. Pflugers Arch 457, 635-644, doi:10.1007/s00424-008-0470-0 (2009).
15. Banerjee, M., Duan, Q. & Xie, Z. SH2 Ligand-Like Effects of Second Cytosolic Domain of Na/K-ATPase alpha1 Subunit on Src Kinase. PloS one 10, e0142119, doi:10.1371/journal.pone.0142119 (2015).
16. Xie, J. et al. Expression of rat NaK-ATPase a2 enables ion pumping but not ouabain-induced signaling in al-deficient porcine renal epithelial cells. Am J Physiol 309, 373-382, doi:10.1152/ajpcell.00103.2015 (2015).
17. Madan, N. et al. Src-independent ERK signaling through the rat alpha3 isoform of Na/K-ATPase. American journal of physiology. Cell physiology 312, C222-c232, doi: 10.1152/ajpcell.00199.2016 (2017).
18. Songyang, Z. et al. SH2 domains recognize specific phosphopeptide sequences. Cell 72, 767-778 (1993).
19. Klinghoffer, R. A., Sachsenmaier, C., Cooper, J. A. & Soriano, P. Src family kinases are required for integrin but not PDGFR signal transduction. The EMBO journal 18, 2459-2471, doi:10.1093/emboj/18.9.2459 (1999).
20. Feraille, E. et al. Insulin-induced stimulation of Na+,K (+)-ATPase activity in kidney proximal tubule cells depends on phosphorylation of the alpha-subunit at Tyr-10. Molecular biology of the cell 10, 2847-2859 (1999).
21. Playford, M. P. & Schaller, M. D. The interplay between Src and integrins in normal and tumor biology. Oncogene 23, 7928-7946, doi:10.1038/sj.onc.1208080 (2004).
22. Lai, F. et al. Identification of a mutant alpha1 Na/K-ATPase that pumps but is defective in signal transduction. The Journal of biological chemistry 288, 13295-13304, doi:10.1074/jbc.M113.467381 (2013).
23. Sato, K. Cellular functions regulated by phosphorylation of EGFR on Tyr845. International journal of molecular sciences 14, 10761-10790, doi:10.3390/ijms140610761 (2013).
24. TeSlaa, T. & Teitell, M. A. Techniques to monitor glycolysis. Methods in enzymology 542, 91-114, doi: 10.1016/b978-0-12-416618-9.00005-4 (2014).
25. Levine, A. J. & Puzio-Kuter, A. M. The control of the metabolic switch in cancers by oncogenes and tumor suppressor genes. Science (New York, N.Y.) 330, 1340-1344, doi:10.1126/science.1193494 (2010).
26. Bertram, J. S. The molecular biology of cancer. Molecular aspects of medicine 21, 167-223 (2000).
27. Grander, D. How do mutated oncogenes and tumor suppressor genes cause cancer? Medical oncology (Northwood, London, England) 15, 20-26 (1998).
28. Hitosugi, T. et al. Tyrosine phosphorylation inhibits PKM2 to promote the Warburg effect and tumor growth. Science signaling 2, ra73, doi:10.1126/scisignal.2000431 (2009).
29. Lunt, S. Y. & Vander Heiden, M. G. Aerobic glycolysis: meeting the metabolic requirements of cell proliferation. Annual review of cell and developmental biology 27, 441-464, doi:10.1146/annurev-cellbio-092910-154237 (2011).
30. Barthel, A. et al. Regulation of GLUT1 gene transcription by the serine/threonine kinase Akt1. The Journal of biological chemistry 274, 20281-20286 (1999).
31. Vander Heiden, M. G. et al. Growth factors can influence cell growth and survival through effects on glucose metabolism. Molecular and cellular biology 21, 5899-5912 (2001).
32. Wieman, H. L., Wofford, J. A. & Rathmell, J. C. Cytokine stimulation promotes glucose uptake via phosphatidylinositol-3 kinase/Akt regulation of Glut1 activity and trafficking. Molecular biology of the cell 18, 1437-1446, doi:10.1091/mbc.E06-07-0593 (2007).
33. Glossmann, H., Presek, P. & Eigenbrodt, E. Association of the src-gene product of Rous sarcoma virus with a pyruvate-kinase inactivation factor. Molecular and cellular endocrinology 23, 49-63 (1981).
34. Koh, C. M. et al. MYC and Prostate Cancer. Genes & cancer 1, 617-628, doi:10.1177/1947601910379132 (2010).
35. Ward, P. S. & Thompson, C. B. Metabolic reprogramming: a cancer hallmark even warburg did not anticipate. Cancer cell 21, 297-308, doi:10.1016/j.ccr.2012.02.014 (2012).
36. Normanno, N. et al. Epidermal growth factor receptor (EGFR) signaling in cancer. Gene 366, 2-16, doi:10.1016/j.gene.2005.10.018 (2006).
37. Samatar, A. A. & Poulikakos, P. I. Targeting RAS-ERK signalling in cancer: promises and challenges. Nature reviews. Drug discovery 13, 928-942, doi:10.1038/nrd4281 (2014).
38. Wang, Y. et al. TRIB1 promotes colorectal cancer cell migration and invasion through activation MMP-2 via FAK/Src and ERK pathways. Oncotarget 8, 47931-47942, doi:10.18632/oncotarget.18201 (2017).
39. Dvela-Levitt, M. et al. Reduction in maternal circulating ouabain impairs offspring growth and kidney development. Journal of the American Society of Nephrology: JASN 26, 1103-1114, doi:10.1681/asn.2014020130 (2015).
40. Liu, J. et al. Impairment of Na/K-ATPase signaling in renal proximal tubule contributes to Dahl salt-sensitive hypertension. The Journal of biological chemistry 286, 22806-22813, doi:10.1074/jbc.M111.246249 (2011).
41. Sodhi, K. et al. pNaKtide Inhibits Na/K-ATPase Reactive Oxygen Species Amplification and Attenuates Adipogenesis. Science advances Vol. 1, no. 9 (2015).
42. Sodhi, K. et al. pNaKtide Attenuates Steatohepatitis and Atherosclerosis by Blocking Na/K-ATPase/ROS Amplification in C57Bl6 and ApoE Knockout Mice Fed a Western Diet. 7, 193, doi:10.1038/s41598-017-00306-5 (2017).
43. Liu, J. et al. Attenuation of Na/K-ATPase Mediated Oxidant Amplification with pNaKtide Ameliorates Experimental Uremic Cardiomyopathy Nature Communications (2016).
44. Kennedy, D. J. et al. CD36 and Na/K-ATPase-alpha1 form a proinflammatory signaling loop in kidney. Hypertension (Dallas, Tex.: 1979) 61, 216-224, doi:10.1161/hypertensionaha.112.198770 (2013).
45. Chen, Y. et al. Oxidized LDL-bound CD36 recruits an Na+/K+-ATPase-Lyn complex in macrophages that promotes atherosclerosis. Science signaling 8, ra91, doi:10.1126/scisignal.aaa9623 (2015).
46. Xie, J. F. et al. Na/K-ATPase/Src complex mediates regulation of CD40 in renal parenchyma. Nephr Dial Transplan (2017).
47. Shvartsman, D. E. et al. Src kinase activity and SH2 domain regulate the dynamics of Src association with lipid and protein targets. The Journal of cell biology 178, 675-686, doi:10.1083/jcb.200701133 (2007).
48. Sakai, H. et al. Up-regulation of Na(+),K(+)-ATPase alpha 3-isoform and down-regulation of the alpha1-isoform in human colorectal cancer. FEBS letters 563, 151-154, doi:10.1016/S0014-5793(04)00292-3S0014579304002923 [pii] (2004).
49. Baker Bechmann, M. et al. Na,K-ATPase Isozymes in Colorectal Cancer and Liver Metastases. Frontiers in physiology 7, 9, doi:10.3389/fphys.2016.00009 (2016).
50. Salyer, S. A. et al. Vacuolar ATPase driven potassium transport in highly metastatic breast cancer cells. Biochimica et biophysica acta 1832, 1734-1743, doi:10.1016/j.bbadis.2013.04.023 (2013).
51. Uhlen, M. et al. Proteomics. Tissue-based map of the human proteome. Science (New York, N.Y.) 347, 1260419, doi:10.1126/science.1260419 (2015).
52. Li, Z. et al. Na/K-ATPase mimetic pNaKtide peptide inhibits the growth of human cancer cells. The Journal of biological chemistry 286, 32394-32403, doi:10.1074/jbc.M110.207597 (2011).
53. Talamonti, M. S., Roh, M. S., Curley, S. A. & Gallick, G. E. Increase in activity and level of pp60c-src in progressive stages of human colorectal cancer. The Journal of clinical investigation 91, 53-60, doi:10.1172/jci116200 (1993).
54. Hiscox, S. et al. Elevated Src activity promotes cellular invasion and motility in tamoxifen resistant breast cancer cells. Breast cancer research and treatment 97, 263-274, doi:10.1007/s10549-005-9120-9 (2006).
55. Kunte, D. P. et al. Down-regulation of the tumor suppressor gene C-terminal Src kinase: an early event during premalignant colonic epithelial hyperproliferation. FEBS letters 579, 3497-3502, doi:10.1016/j.febslet.2005.05.030 (2005).
56. Mathieu, V. et al. The Sodium Pump alpha1 Subunit: a Disease Progression-Related Target for Metastatic Melanoma Treatment. Journal of cellular and molecular medicine, doi:JCMM708 [pii]10.1111/j.1582-4934.2009.00708.x (2009).
57. Hanahan, D. & Weinberg, R. A. Hallmarks of cancer: the next generation. Cell 144, 646-674, doi:10.1016/j.cell.2011.02.013 (2011).
58. Hanahan, D. & Weinberg, R. A. The hallmarks of cancer. Cell 100, 57-70, doi:S0092-8674(00)81683-9 [pii] (2000).
59. Tian, J. et al. Changes in sodium pump expression dictate the effects of ouabain on cell growth. The Journal of biological chemistry 284, 14921-14929, doi: M808355200 [pii]10.1074/jbc. M808355200 (2009).
60. Barker, S. B. & Summerson, W. H. The colorimetric determination of lactic acid in biological material. Journal of Biological Chemistry 138, 535-554 (1941).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for identifying a cancer cell, comprising:
obtaining a biological sample from a subject, the biological sample including one or more cells;
assaying for a reduction in an amount of a phosphorylation at a Y260 residue in a Na/K ATPase present in the one more cells in the biological sample relative to a control level of a Y260 phosphorylation present in one or more cells in a biological sample obtained from a healthy subject,
detecting a metabolic switch from oxidative phosphorylation to aerobic glycolysis in the one or more cells in the biological sample, detecting the metabolic switch comprising assaying for an increase in an amount of lactate present in the one or more cells in the biological sample relative to a control level of lactate present in a biological sample from a healthy subject, and
identifying the biological sample as including one or more cancer cells if there is a reduction in the amount of phosphorylation at the Y260 residue and an increase in lactate present in the one or more cells.

2. The method of claim 1, wherein the Na/K ATPase is an α1 Na/K ATPase isoform.

3. The method of claim 1, wherein the biological sample comprises a tumor biopsy.

4. The method of claim 1, wherein the cancer is a prostate cancer or a breast cancer.

5. The method of claim 1, wherein the cancer is a metastatic cancer.

6. The method of claim 1, wherein determining an amount of phosphorylation at a Y260 residue comprises determining an amount of phosphorylation using mass spectrometry (MS) analysis, immunoassay analysis, or both.

7. The method of claim 1, wherein the subject is human.

8. The method of claim 1, further comprising a step of measuring an amount of Src activity in the biological sample.

9. The method of claim 1, further comprising administering a chemotherapeutic agent to the subject subsequent to assaying for a reduction in the amount of the phosphorylation at the Y260 residue in the Na/K ATPase present in the biological sample obtained from the subject.

* * * * *